(12) United States Patent
Shirai et al.

(10) Patent No.: US 7,750,155 B2
(45) Date of Patent: Jul. 6, 2010

(54) PYRAZINYL HYDROXYACRYLAMIDE COMPOUNDS HAVING AN INHIBITORY EFFECT ON THE ACTIVITY OF HISTONE DEACETYLASE

(75) Inventors: Fumiyuki Shirai, Tokyo (JP); Hideo Tsutsumi, Osaka (JP); Hiromichi Itani, Hyogo (JP); Yoshihiro Kozuki, Tokyo (JP); Yoshiteru Eikyu, Tokyo (JP); Taro Masunaga, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 12/278,580

(22) PCT Filed: Feb. 6, 2007

(86) PCT No.: PCT/JP2007/052447
§ 371 (c)(1), (2), (4) Date: Aug. 7, 2008

(87) PCT Pub. No.: WO2007/091703
PCT Pub. Date: Aug. 16, 2007

(65) Prior Publication Data
US 2009/0054465 A1   Feb. 26, 2009

(30) Foreign Application Priority Data
Feb. 7, 2006   (AU) ............................... 2006900588

(51) Int. Cl.
   *C07D 241/02* (2006.01)
(52) U.S. Cl. ................... 544/336; 546/210; 548/557
(58) Field of Classification Search ................. 544/336; 546/210; 548/557
   See application file for complete search history.

(56) References Cited

U.S. PATENT DOCUMENTS

| | | |
|---|---|---|
| 6,511,990 B1 | 1/2003 | Breslow et al. |
| 7,135,493 B2 | 11/2006 | Urano et al. |
| 7,465,731 B2 | 12/2008 | Ishibashi et al. |
| 7,557,127 B2 | 7/2009 | Ishibashi et al. |
| 2004/0087631 A1 | 5/2004 | Bacopoulos et al. |
| 2004/0092558 A1 | 5/2004 | Klimko et al. |

FOREIGN PATENT DOCUMENTS

| | | |
|---|---|---|
| WO | WO 93/12075 A1 | 6/1993 |
| WO | WO 95/13264 A1 | 5/1995 |
| WO | WO 97/24117 A1 | 7/1997 |
| WO | WO 01/38322 A1 | 5/2001 |
| WO | 02 22577 | 3/2002 |
| WO | WO 02/18326 A1 | 3/2002 |
| WO | WO 02/22577 A2 | 3/2002 |
| WO | WO 02/24653 A1 | 3/2002 |
| WO | WO 02/30872 A1 | 4/2002 |
| WO | WO 02/074298 A1 | 9/2002 |
| WO | WO 03/082288 A1 | 10/2003 |
| WO | WO 03/087066 A1 | 10/2003 |
| WO | WO 2004/024160 A1 | 3/2004 |
| WO | 2004 063169 | 7/2004 |
| WO | WO 2004/063169 A1 | 7/2004 |
| WO | 2005 065681 | 7/2005 |
| WO | WO 2005/065681 A1 | 7/2005 |
| WO | WO 2005/086898 A2 | 9/2005 |
| WO | 2006 016680 | 2/2006 |
| WO | WO 2006/016680 A1 | 2/2006 |

OTHER PUBLICATIONS

U.S. Appl. No. 12/538,413, filed Aug. 10, 2009, Shirai, et al.

*Primary Examiner*—James O Wilson
*Assistant Examiner*—Douglas M Willis
(74) *Attorney, Agent, or Firm*—Oblon, Spivak, McClelland, Maier & Neustadt, L.L.P.

(57) ABSTRACT

This invention relates to novel N-hydroxyacrylamide compounds of formula (I) and pharmaceutically acceptable salts thereof. More particularly, it relates to novel N-hydroxyacrylamide compounds and pharmaceutically acceptable salts thereof which act as a HDAC inhibitor, to a pharmaceutical composition comprising the same and to a method of using the same therapeutically in the treatment and/or prevention of HDAC-related disease.

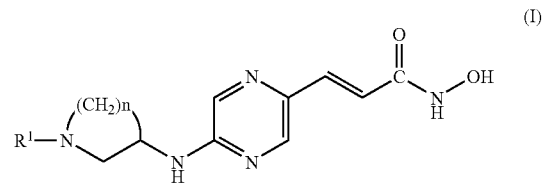

(I)

30 Claims, No Drawings

PYRAZINYL HYDROXYACRYLAMIDE COMPOUNDS HAVING AN INHIBITORY EFFECT ON THE ACTIVITY OF HISTONE DEACETYLASE

TECHNICAL FIELD

The present invention relates to a compound useful as a medicament, and to a pharmaceutical composition comprising the same.

BACKGROUND ART

Histone deacetylase (hereinafter also referred to as HDAC) is known to play an essential role in the transcriptional machinery for regulating gene expression, induce histone hyperacetylation and to affect the gene expression. Therefore, it is useful as a therapeutic or prophylactic agent for diseases caused by abnormal gene expression such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

Many compounds which can inhibit the functions of the enzymes (HDAC inhibitors) has been studied extensively (see, e.g., WO01/38322, WO02/22577, WO2004/024160, US2004/0087631, WO2004/063169, US2004/0092558, WO2005/086898 etc).

For example, WO 01/38322 discloses an inhibitor of histone deacetylase represented by the following formula:

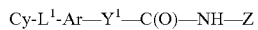

wherein

Cy is cycloalkyl, aryl, heteroaryl or heterocyclyl, each of which is optionally substituted;

$L^1$ is $—(CH_2)_m—W—$ wherein m is an integer of 0 to 4, and W is selected from the group consisting of $—C(O)NH—$, $—S(O)_2NH—$, etc.;

Ar is optionally substituted arylene, which is optionally fused to an aryl, heteroaryl ring, etc.;

$Y^1$ is a chemical bond or a straight- or branched-chain saturated alkylene, wherein said alkylene is optionally substituted; and Z is selected from the group consisting of anilinyl, pyridyl, thiadiazolyl and —O-M wherein M is H or a pharmaceutically acceptable cation.

WO 02/22577 discloses the following hydroxamate compound as a deacetylase inhibitor:

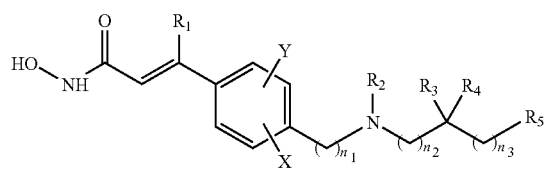

wherein $R_1$ is H, halo or a straight chain $C_1$-$C_6$ alkyl;

$R_2$ is selected from H, $C_1$-$C_{10}$ alkyl, $C_4$-$C_9$ cycloalkyl, $C_4$-$C_9$ heterocycloalkyl, $C_4$-$C_9$ heterocycloalkylalkyl, cycloalkylalkyl, aryl, heteroaryl, etc.;

$R_3$ and $R_4$ are the same or different and independently H, $C_1$-$C_6$ alkyl, acyl or acylamino, or $R_3$ and $R_4$ together with the carbon to which they are bound to represent C=O, C=S, etc., or $R_2$ together with the nitrogen to which it is bound and $R_3$ together with the carbon to which it is bound to form a $C_4$-$C_9$ heterocycloalkyl, a heteroaryl, a polyheteroaryl, a non-aromatic polyheterocycle, or a mixed aryl and non-aryl polyheterocycle ring;

$R_5$ is selected from H, $C_1$-$C_6$ alkyl, etc.;

n, $n_1$, $n_2$ and $n_3$ are the same or different and independently selected from 0-6, when $n_1$ is 1-6, each carbon atom can be optionally and independently substituted with $R_3$ and/or $R_4$;

X and Y are the same or different and independently selected from H, halo, $C_1$-$C_4$ alkyl, etc.;

or a pharmaceutically acceptable salt thereof.

SUMMARY OF THE INVENTION

The present invention relates to a novel compound useful as a medicament, and to a pharmaceutical composition comprising the same.

More particularly, the present invention relates to a compound having a potent inhibitory effect on the activity of histone deacetylase.

The inventors of the present invention have also found that histone deacetylase inhibitors, such as a compound of the formula (I) (hereinafter compound (I)), have a potent immunosuppressive effect and potent antitumor effect. Therefore, a histone deacetylase inhibitors such as compound (I) is useful as an active ingredient for an immunosuppressant and an antitumor agent, and useful as an active ingredient for a therapeutic or prophylactic agent for diseases such as inflammatory disorders, diabetes, diabetic complications, homozygous thalassemia, fibrosis, cirrhosis, acute promyelocytic leukaemia (APL), organ transplant rejections, autoimmune diseases, protozoal infections, tumors, etc.

Accordingly, one object of the present invention is to provide a compound having biological activities for treating or preventing the diseases as stated above.

A further object of the present invention is to provide a pharmaceutical composition containing the compound (I) as an active ingredient.

A yet further object of the present invention is to provide use of the histone deacetylase inhibitors, such as compound (I), for treating and preventing the diseases as stated above.

A yet further object of the present invention is to provide a commercial package comprising the pharmaceutical composition containing the compound (I) and a written matter associated therewith, the written matter stating that the pharmaceutical composition may or should be used for treating or preventing the diseases as stated above.

Thus, the present invention provides a compound having the following formula (I):

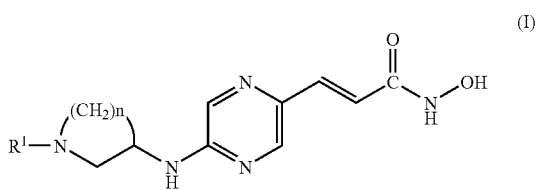

wherein

R[1] is cyclopentylmethyl, cyclopentylethyl, cyclohexylmethyl, cyclohexylethyl, cyclohexylpropyl, benzyl, phenethyl, phenylpropyl, 2-methyl-2-phenylpropyl, naphthylmethyl, thienylethyl or 7-oxabicyclo[2.2.1]heptylmethyl, each of which may be substituted with one or more substituent(s) selected from the group consisting of fluoro, chloro, bromo, methoxy, dimethylamino and hydroxymethyl, n is 2 or 3, or a pharmaceutically acceptable salt thereof.

The above-mentioned compound or a pharmaceutically acceptable salt thereof can be prepared by the process as illustrated in the following reaction scheme or by the methods disclosed in the Preparations and Examples.

In the above and subsequent descriptions of the present specification, suitable examples and illustration of the various definitions which the present invention intends to include within the scope thereof are explained in detail as follows.

The compound (I) of the present invention is obtained from compound (A), for example, according to the following process or methods disclosed in the Examples.

Process 1

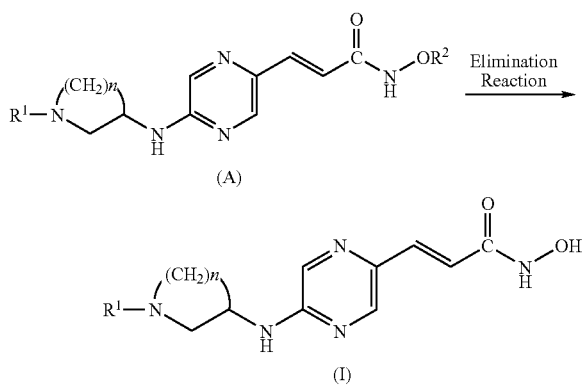

wherein R[1] and n are as defined above, and

R[2] is hydroxy protecting group.

Process 1

The compound (I) is obtained by subjecting the compound (A) to the elimination reaction of hydroxy protecting group in the presence of an acid.

The acid includes such as hydrogen chloride solution (e.g. hydrogen chloride in solvent such as methanol, dioxane, ethyl acetate, diethyl ether, etc.), acetic acid, p-toluenesulfonic acid, boric acid, etc.

Optionally, one or more suitable solvent(s) for the deprotection is (are) used. Such solvent includes such as methanol, ethanol, ethyl acetate, dioxane, diethyl ether, acetic acid, etc.

The temperature of the reaction is not critical, and the reaction is usually carried out from under cooling to heating.

The compound (I) may be a pharmaceutically acceptable salt, which is also encompassed in the scope of the present invention. For example, when a basic group such as an amino group is present in a molecule, the salt is exemplified by an acid addition salt (e.g. salt with an inorganic acid such as hydrochloric acid, hydrobromic acid, sulfuric acid, etc., salt with an organic acid such as methanesulfonic acid, benzenesulfonic acid, 4-toluenesulfonic acid, camphorsulfonic acid (e.g., [(1S,4R)-7,7-dimethyl-2-oxobicyclo[2.2.1]hept-1-yl] methanesulfonic acid or an enantiomer thereof, etc.), fumaric acid, maleic acid, mandelic acid, citric acid, salicylic acid, malonic acid, glutaric acid, succinic acid, etc.), etc., and when an acidic group such as carboxyl group is present, the salt is exemplified by a basic salt (e.g. salt with a metal such as lithium, sodium, potassium, calcium, magnesium, aluminium, etc., a salt with amino acid such as lysine, etc.), etc.

In addition, solvates (e.g. hydrate, ethanolate, etc.), anhydrous forms and other polymorphic forms or pharmaceutically acceptable salts of the compound (I) are also encompassed in the scope of the present invention.

When the compound (I) has stereoisomers based on asymmetric carbon atom(s) or double bond(s), such as an optically active form, a geometric isomer and the like, such isomers and mixtures thereof are also encompassed in the scope of the present invention.

It is also to be noted that pharmaceutical acceptable prodrugs of the compound (I) are included within the scope of the present invention. Pharmaceutical acceptable prodrug means compound having functional groups which can be converted to —COOH, —NH$_2$, —OH etc in physiological condition to form the compound (I) of the present invention.

In the above and subsequent descriptions of the present specification, suitable examples and illustration of the various definitions which the present invention intends to include within the scope thereof are explained in detail as follows.

Suitable "hydroxy protecting group" is as follows:

lower alkyl (e.g., methyl, ethyl, propyl, isopropyl, butyl, isobutyl, t-butyl, pentyl, hexyl, etc.), preferably methyl; lower alkoxy(lower)alkyl (e.g. methoxymethyl, etc.); lower alkoxy(lower)alkoxy(lower)alkyl (e.g. 2-methoxyethoxymethyl, etc.);

ar(lower)alkyl in which the aryl portion is optionally substituted with one or more suitable substituent (s) (e.g. benzyl (Bn), p-methoxybenzyl, m,p-dimethoxybenzyl, etc.), preferably benzyl;

ar(lower)alkoxy(lower)alkyl in which the aryl portion is optionally substituted with one or more suitable substituent(s) (e.g. benzyloxymethyl, p-methoxybenzyloxymethyl, etc.); (lower)alkylthio(lower)alkyl (e.g. methylthiomethyl, ethylthiomethyl, propylthiomethyl, isopropylthiomethyl, butylthiomethyl, isobutylthiomethyl, hexylthiomethyl, etc.), etc., preferably methylthiomethyl;

trisubstituted silyl such as tri(lower)alkylsilyl (e.g. trimethylsilyl, triethylsilyl, tributylsilyl, tert-butyldimethylsilyl, tritert-butylsilyl, etc.), lower alkyldiarylsilyl (e.g. methyldiphenylsilyl, ethyldiphenylsilyl, propyldiphenylsilyl, tert-butyldiphenylsilyl (TBDPS), etc.), etc., preferably tert-butyldimethylsilyl (TBDMS) and tert-butyldiphenylsilyl;

heterocyclic group (e.g. tetrahydropyranyl, etc.);

acyl as described below [e.g. aliphatic acyl such as lower alkanoyl (e.g. acetyl, propanoyl, pivaloyl, etc.); aromatic acyl (e.g. benzoyl (Bz), toluoyl, naphthoyl, fluorenylcarbonyl, etc.);

lower alkoxy-carbonyl (e.g. methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, etc.), etc.;

ar(lower)alkoxycarbonyl in which the aryl portion is optionally substituted with one or more suitable substituent(s) (e.g. benzyloxycarbonyl, bromobenzyloxycarbonyl, etc.); lower alkylsulfonyl (e.g. methylsulfonyl, ethylsulfonyl, etc.); lower alkoxysulfonyl (e.g. methoxysulfonyl, ethoxysulfonyl, etc.);

ar(lower)alkanoyl (e.g. phenylacetyl, phenylpropanoyl, phenylbutanoyl, phenylisobutanoyl, phenylpentanoyl, phenylhexanoyl, naphthylacetyl, naphthylpropanoyl, naphthylbutanoyl, naphthylisobutanoyl, naphthylpentanoyl, naphthylhexanoyl, etc.);

ar(lower)alkenoyl such as ar ($C_3$-$C_6$)alkenoyl (e.g. phenylpropenoyl, phenylbutenoyl, phenylmethacryloyl, phenylpentenoyl, phenylhexenoyl, naphthylpropenoyl, naphthylbutenoyl, naphthylmethacryloyl, naphthylpentenoyl, naphthylhexenoyl, etc.), etc.];

lower alkenyl (e.g. vinyl, allyl, etc.); etc.

The preferable hydroxy protecting group for the present invention is, for example, tetrahydropyranyl, trimethylsilyl, t-butyldimethylsilyl, etc.

The preferred embodiment of the present invention is shown as follow.

In the compound having the formula (I), $R^1$ is preferably cyclopentylmethyl, fluoro(methoxy)benzyl, dimethylaminobenzyl, and more preferably, the compound is selected from the group consisting of:
(2E)-3-(5-{[(3R)-1-(cyclopentylmethyl)-3-pyrrolidinyl]amino}-2-pyrazinyl)-N-hydroxyacrylamide dihydrochloride,
(2E)-3-[5-({(3R)-1-[2-(dimethylamino)benzyl]-3-pyrrolidinyl}amino)-2-pyrazinyl]-N-hydroxyacrylamide trihydrochloride,
(2E)-3-(5-{[(3R)-1-(4-fluoro-3-methoxybenzyl)-3-pyrrolidinyl]amino}-2-pyrazinyl)-N-hydroxyacrylamide dihydrochloride and
(2E)-3-(5-{[(3R)-1-(5-fluoro-2-methoxybenzyl)-3-pyrrolidinyl]amino}-2-pyrazinyl)-N-hydroxyacrylamide dihydrochloride, or $R^1$ is preferably cyclopentylethyl, [(hydroxymethyl)cyclohexyl]methyl, cyclohexylethyl, cyclohexylpropyl, fluorophenethyl, difluorophenethyl, chlorophenethyl, bromophenethyl, methoxyphenethyl, phenylpropyl, 2-methyl-2-phenylpropyl, naphthylmethyl, thienylethyl or 7-oxabicyclo[2.2.1]heptylmethyl, and more preferably, the compound is selected from the group consisting of:
(2E)-3-(5-{[(3R)-1-(2-cyclopentylethyl)-3-pyrrolidinyl]amino}-2-pyrazinyl)-N-hydroxyacrylamide dihydrochloride,
(2E)-3-(5-{[(3R)-1-(2-cyclopentylethyl)-3-piperidinyl]amino}-2-pyrazinyl)-N-hydroxyacrylamide dihydrochloride,
(2E)-N-hydroxy-3-(5-{[(3R)-1-{[1-(hydroxymethyl)cyclohexyl]methyl}-3-pyrrolidinyl]amino}-2-pyrazinyl)acrylamide dihydrochloride,
(2E)-3-(5-{[(3R)-1-(2-cyclohexylethyl)-3-pyrrolidinyl]amino}-2-pyrazinyl)-N-hydroxyacrylamide dihydrochloride,
(2E)-3-(5-{[(3R)-1-(2-cyclohexylethyl)-3-piperidinyl]amino}-2-pyrazinyl)-N-hydroxyacrylamide dihydrochloride,
(2E)-3-(5-{[(3R)-1-(3-cyclohexylpropyl)-3-pyrrolidinyl]amino}-2-pyrazinyl)-N-hydroxyacrylamide dihydrochloride,
(2E)-3-[5-({(3R)-1-[2-(3-fluorophenyl)ethyl]-3-pyrrolidinyl}amino)-2-pyrazinyl]-N-hydroxyacrylamide dihydrochloride,
(2E)-3-[5-({(3R)-1-[2-(3-fluorophenyl)ethyl]-3-piperidinyl}amino)-2-pyrazinyl]-N-hydroxyacrylamide dihydrochloride,
(2E)-3-[5-({(3R)-1-[2-(2-fluorophenyl)ethyl]-3-piperidinyl}amino)-2-pyrazinyl]-N-hydroxyacrylamide dihydrochloride,
(2E)-3-[5-({(3R)-1-[2-(2,4-difluorophenyl)ethyl]-3-pyrrolidinyl}amino)-2-pyrazinyl]-N-hydroxyacrylamide dihydrochloride,
(2E)-3-[5-({(3R)-1-[2-(2,6-difluorophenyl)ethyl]-3-pyrrolidinyl}amino)-2-pyrazinyl]-N-hydroxyacrylamide dihydrochloride,
(2E)-3-[5-({(3R)-1-[2-(3,4-difluorophenyl)ethyl]-3-pyrrolidinyl}amino)-2-pyrazinyl]-N-hydroxyacrylamide dihydrochloride,
(2E)-3-[5-({(3R)-1-[2-(2,4-difluorophenyl)ethyl]-3-piperidinyl}amino)-2-pyrazinyl]-N-hydroxyacrylamide dihydrochloride,
(2E)-3-[5-({(3R)-1-[2-(3,4-difluorophenyl)ethyl]-3-piperidinyl}amino)-2-pyrazinyl]-N-hydroxyacrylamide dihydrochloride,
(2E)-3-[5-({(3R)-1-[2-(2-chlorophenyl)ethyl]-3-pyrrolidinyl}amino)-2-pyrazinyl]-N-hydroxyacrylamide dihydrochloride,
(2E)-3-[5-({(3R)-1-[2-(4-chlorophenyl)ethyl]-3-pyrrolidinyl}amino)-2-pyrazinyl]-N-hydroxyacrylamide dihydrochloride,
(2E)-3-[5-({(3R)-1-[2-(2-chlorophenyl)ethyl]-3-piperidinyl}amino)-2-pyrazinyl]-N-hydroxyacrylamide dihydrochloride,
(2E)-3-[5-({(3R)-1-[2-(4-chlorophenyl)ethyl]-3-piperidinyl}amino)-2-pyrazinyl]-N-hydroxyacrylamide dihydrochloride,
(2E)-3-[5-({(3R)-1-[2-(4-bromophenyl)ethyl]-3-pyrrolidinyl}amino)-2-pyrazinyl]-N-hydroxyacrylamide dihydrochloride,
(2E)-N-hydroxy-3-[5-({(3R)-1-[2-(4-methoxyphenyl)ethyl]-3-pyrrolidinyl}amino)-2-pyrazinyl]acrylamide dihydrochloride,
(2E)-N-hydroxy-3-(5-{[(3R)-1-(3-phenylpropyl)-3-piperidinyl]amino}-2-pyrazinyl)acrylamide dihydrochloride,
(2E)-N-hydroxy-3-(5-{[(3R)-1-(2-methyl-2-phenylpropyl)-3-pyrrolidinyl]amino}-2-pyrazinyl)acrylamide dihydrochloride
(2E)-N-hydroxy-3-(5-{[(3R)-1-(1-naphthylmethyl)-3-pyrrolidinyl]amino}-2-pyrazinyl)acrylamide dihydrochloride,
(2E)-N-hydroxy-3-[5-({(3R)-1-[2-(2-thienyl)ethyl]-3-pyrrolidinyl}amino)-2-pyrazinyl]acrylamide dihydrochloride, and
(2E)-N-hydroxy-3-(5-{[(3R)-1-(7-oxabicyclo[2.2.1]hept-1-ylmethyl)-3-pyrrolidinyl]amino}-2-pyrazinyl)acrylamide dihydrochloride, and most preferably, $R^1$ is fluorophenethyl, difluorophenethyl or chlorophenetyl, and the compound is selected from the group consisting of:

(2E)-3-[5-({(3R)-1-[2-(3-fluorophenyl)ethyl]-3-pyrrolidinyl}amino)-2-pyrazinyl]-N-hydroxyacrylamide dihydrochloride,
(2E)-3-[5-({(3R)-1-[2-(3-fluorophenyl)ethyl]-3-piperidinyl}amino)-2-pyrazinyl]-N-hydroxyacrylamide dihydrochloride,
(2E)-3-[5-({(3R)-1-[2-(2-fluorophenyl)ethyl]-3-piperidinyl}amino)-2-pyrazinyl]-N-hydroxyacrylamide dihydrochloride,
(2E)-3-[5-({(3R)-1-[2-(2,4-difluorophenyl)ethyl]-3-pyrrolidinyl}amino)-2-pyrazinyl]-N-hydroxyacrylamide dihydrochloride,
(2E)-3-[5-({(3R)-1-[2-(2,6-difluorophenyl)ethyl]-3-pyrrolidinyl}amino)-2-pyrazinyl]-N-hydroxyacrylamide dihydrochloride,
(2E)-3-[5-({(3R)-1-[2-(3,4-difluorophenyl)ethyl]-3-pyrrolidinyl}amino)-2-pyrazinyl]-N-hydroxyacrylamide dihydrochloride,
(2E)-3-[5-({(3R)-1-[2-(2,4-difluorophenyl)ethyl]-3-piperidinyl}amino)-2-pyrazinyl]-N-hydroxyacrylamide dihydrochloride,
(2E)-3-[5-({(3R)-1-[2-(3,4-difluorophenyl)ethyl]-3-piperidinyl}amino)-2-pyrazinyl]-N-hydroxyacrylamide dihydrochloride,
(2E)-3-[5-({(3R)-1-[2-(2-chlorophenyl)ethyl]-3-pyrrolidinyl}amino)-2-pyrazinyl]-N-hydroxyacrylamide dihydrochloride,
(2E)-3-[5-({(3R)-1-[2-(4-chlorophenyl)ethyl]-3-pyrrolidinyl}amino)-2-pyrazinyl]-N-hydroxyacrylamide dihydrochloride,
(2E)-3-[5-({(3R)-1-[2-(2-chlorophenyl)ethyl]-3-piperidinyl}amino)-2-pyrazinyl]-N-hydroxyacrylamide dihydrochloride and
(2E)-3-[5-({(3R)-1-[2-(4-chlorophenyl)ethyl]-3-piperidinyl}amino)-2-pyrazinyl]-N-hydroxyacrylamide dihydrochloride.

The following abbreviations are also used in the present specification: HOBT or HOBt (1-hydroxybenzotriazole); NBS (N-bromosuccinimide); WSCD (1-ethyl-3-(3'-dimethylaminopropyl) carbodiimide); WSCD-HCl or EDCI (1-ethyl-3-(3'-dimethylaminopropyl) carbodiimide hydrochloride); DMF (N,N-dimethylformamide); DMA (N,N-dimethylacetamide); aq. (aqueous solution); MeOH (methanol); MeCN (acetonitrile) Et₃N (triethylamine); EtOH (ethanol); IPE (diisopropyl ether); tBu (t-butyl); AcOEt (ethyl acetate); DIEA (diisopropylethylamine); DIBAL (diisobutylaluminium hydride); THF (tetrahydrofuran) and NaH (sodium hydride).

Test Method

In order to show the usefulness of the compound (I) of the invention, the pharmacological test result of the representative compound of the present invention is shown in the following.

Test 1: Determination of Histone Deacetylase Inhibitor Activity

The partial purification of human histone deacetylase, the preparation of [$^3$H] acetyl histones, and the assay for histone deacetylase activity were performed basically according to the method as proposed by Yoshida et al. as follows.

Partial Purification of Human Histone Deacetylase

The human histone deacetylase was partially purified from human T cell leukemia Jurkat cells. Jurkat cells ($5 \times 10^8$ cells) were suspended in 40 mL of the HDA buffer consisting of 15 mM potassium phosphate, pH 7.5, 5% glycerol and 0.2 mM EDTA. After homogenization, nuclei were collected by centrifugation ($35,000 \times g$, 10 min) and homogenized in 20 mL of the same buffer supplemented with 1 M $(NH_4)_2SO_4$. The viscous homogenate was sonicated and clarified by centrifugation ($35,000 \times g$, 10 min), and the deacetylase was precipitated by raising the concentration of $(NH_4)_2SO_4$ to 3.5 M. The precipitated protein was dissolved in 10 mL of the HDA buffer and dialyzed against 4 liters of the same buffer. The dialyzate was then loaded onto a DEAE-cellulose (Whatman DE52) column ($25 \times 85$ mm) equilibrated with the same buffer and eluted with 300 mL of a linear gradient (0-0.6 M) of NaCl. A single peak of histone deacetylase activity appeared between 0.3 and 0.4 M NaCl.

Preparation of [$^3$H] Acetyl Histone

To obtain [$^3$H] acetyl-labeled histone as the substrate for the histone deacetylase assay, $1 \times 10^8$ cells of Jurkat in 20 mL of RPMI-1640 medium (supplemented with 10% FBS, penicillin (50 units/mL) and streptomycin (50 µg/mL)) were incubated with 300 MBq [$^3$H] sodium acetate in the presence of 5 mM sodium butyrate for 30 minutes in 5% $CO_2$-95% air atmosphere at 37° C. in a 75 cm$^3$ flask, harvested into a centrifuge tube (50 mL), collected by centrifugation at 1000 rpm for 10 minutes, and washed once with phosphate-buffered saline. The washed cells were suspended in 15 mL of ice-cold lysis buffer (10 mM Tris-HCl, 50 mM sodium bisulfite, 1% Triton X-100, 10 mM $MgCl_2$, 8.6% sucrose, pH 6.5). After Dounce homogenization (30 stroke), the nuclei were collected by centrifugation at 1000 rpm for 10 minutes, washed 3 times with 15 mL of the lysis buffer, and once with 15 mL of ice-cooled washing buffer (10 mM Tris-HCl, 13 mM EDTA, pH 7.4) successively. The pellet was suspended in 6 mL of ice-cooled water using a mixer, and 68 µl of $H_2SO_4$ was added to the suspension to give a concentration of 0.4 N. After incubation at 4° C. for 1 hour, the suspension was centrifuged for 5 minutes at 15,000 rpm, and the supernatant was taken and mixed with 60 mL of acetone. After overnight incubation at -20° C., the coagulated material was collected by microcentrifugation, air-dried, and stored at -80° C.

Assay for Histone Deacetylase Activity

For the standard assay, 10 µl of [$^3$H] acetyl-labeled histones were added to 90 µl of the enzyme fraction, and the mixture was incubated at 25° C. for 30 minutes. The reaction was stopped by addition of 10 µl of HCl. The released [$^3$H] acetic acid was extracted with 1 mL of ethyl acetate, and 0.9 mL of the solvent layer was taken into 10 mL of toluene scintillation solution for determination of radioactivity.

Test 2: Determination of T-Cell Growth Inhibitor Activity

The T lymphocyte blastogenesis test was performed in microtiter plates with each well containing $1.5 \times 10^5$ splenic cells of Lewis rats in 0.1 mL RPMI-1640 medium supplemented with 10% fetal bovine serum (FBS), 50 mM 2-mercaptoethanol, penicilln (100 units/mL) and streptomycin (100 µg/mL), to which Concanavalin A (1 µg/mL) was added. The cells were incubated at 37° C. in a humidified atmosphere of 5% $CO_2$ for 72 hours. After the culture period, suppressive activities of the test compounds in T lymphocyte blastogenesis were quantified by AlamarBlue (trademark) Assay. The test samples were dissolved in DMSO and further diluted with RPMI-1640 medium and added to the culture. The activities of the test compounds were expressed as $IC_{50}$.

The results of those tests are shown in the Table 1.

TABLE 1

HDAC inhibitory activity and T-cell growth inhibitory activity of the compound of the present invention

| Examples | Test 1: HDAC inhibitory activity IC$_{50}$ (nM) | Test 2: T-cell growth inhibitory activity IC$_{50}$ (nM) |
|---|---|---|
| Example 1 | 2.3 | 2.4 |
| Example 2 | 1.5 | 2.3 |
| Example 3 | 2.7 | 1.2 |
| Example 4 | 3.6 | 1.2 |
| Example 5 | 3.3 | 0.93 |
| Example 6 | 1.7 | 0.65 |
| Example 7 | 1.5 | 0.79 |
| Example 8 | 1.7 | 1.1 |
| Example 9 | 1.0 | 1.8 |
| Example 10 | 3.0 | 3.2 |
| Example 11 | 0.95 | 4.5 |
| Example 12 | 0.59 | 2.0 |
| Example 13 | 1.9 | 4.7 |
| Example 14 | 3.8 | 1.2 |
| Example 15 | 4.4 | 6.4 |
| Example 16 | 6.6 | 4.1 |
| Example 17 | 3.3 | 5.0 |
| Example 18 | 2.2 | 2.2 |
| Example 19 | 1.6 | 1.3 |
| Example 20 | 0.79 | 2.1 |
| Example 21 | 0.98 | 2.4 |
| Example 22 | 0.87 | 1.3 |
| Example 23 | 2.0 | 1.7 |
| Example 24 | 0.81 | 2.4 |
| Example 25 | 1.8 | 2.2 |
| Example 26 | 1.4 | 0.44 |
| Example 27 | 0.92 | 0.38 |
| Example 28 | 4.2 | 11 |
| Example 29 | 6.5 | 3.3 |

Test 3: Ames Test

*Salmonella typhimurium* TA98 and TA100 which are histidine auxotrophic mutant are treated with a test substance in the absence or presence of a metabolic activation system for 20 min at 37° C. with shaking, and then the treatment mixture is spread on an agar plate and incubated for about 48 hr at 37° C. Number of revertant colony on each plate is counted and a potential to induce gene mutation of the test substance is evaluated. Result of test, all example compounds of this invention were Ames negative.

Test 4: Measurement of Change Rate of Blood Corpuscles

Experimental drugs were oral administered to rats (male LEW) once a day for continuous 14 days. The blood sample contained heparin and EDTA were collected at 24 hr after last administration, and the number of differential blood corpuscles were measured by auto-hemocytometer (Sysmex).

TABLE 2

The results of blood corpuscles change rate after compound is administered at 4 mg/kg

| | decrease rate (%) | |
|---|---|---|
| Examples | platelet | white blood corpuscle |
| Example 1 | 18.3 | 43.7 |
| Example 5 | 9.4 | 40.3 |
| Example 6 | 24.3 | 72.2 |
| Example 18 | 3.4 | 31.7 |
| Example 19 | 14.2 | 38.1 |
| Example 23 | 18.6 | 64.6 |
| Example 25 | 6.2 | 63.1 |

Thus, the decrease rate of the platelet of the compound of this invention was smaller than the decrease rate of the white blood corpuscle according to the medicinal effect.

As the result of these examinations, it was shown that the compounds of this invention had HDAC inhibitory activity and few side effects.

The pharmaceutical composition of the present invention comprising histone deacetylase inhibitor such as the compound (I) is useful as a therapeutic or prophylactic agent for diseases caused by abnormal gene expression, such as inflammatory disorders, diabetes, diabetic complications, homozygous thalassemia, fibrosis, cirrhosis, acute promyelocytic leukaemia (APL), protozoal infection, etc. Furthermore, it is useful as an antitumor agent or immunosuppressant, which prevents an organ transplant rejection and autoimmune diseases as exemplified below:

rejection reactions by transplantation of organs or tissues such as the heart, kidney, liver, bone marrow, skin, cornea, lung, pancreas, small intestine, limb, muscle, nerve, intervertebral disc, trachea, myoblast, cartilage, etc.;

graft-versus-host reactions following bone marrow transplantation;

autoimmune diseases such as rheumatoid arthritis, systemic lupus erythematosus, Hashimoto's thyroiditis, multiple sclerosis, myasthenia gravis, type I diabetes, etc.; and infections caused by pathogenic microorganisms (e.g. *Aspergillus fumigatus, Fusarium oxysporum, Trichophyton asteroides*, etc.).

Furthermore, pharmaceutical preparations of the histone deacetylase inhibitor, such as the compound (I), are useful for the therapy or prophylaxis of the following diseases.

Inflammatory or hyperproliferative skin diseases or cutaneous manifestations of immunologically-mediated diseases (e.g. psoriasis, atopic dermatitis, contact dermatitis, eczematoid dermatitis, seborrheic dermatitis, lichen planus, pemphigus, bullous pemphigoid, epidermolysis bullbsa, urticaria, angioedema, vasculitides, erythema, dermal eosinophilia, lupus erythematosus, acne, alopecia greata, etc.);

autoimmune diseases of the eye (e.g. keratoconjunctivitis, vernal conjunctivitis, uveitis associated with Behcet's disease, keratitis, herpetic keratitis, conical keratitis, corneal epithelial dystrophy, keratoleukoma, ocular premphigus, Mooren's ulcer, scleritis, Grave's opthalmopathy, Vogt-Koyanagi-Harada syndrome, keratoconjunctivitis sicca (dry eye), phlyctenule, iridocyclitis, sarcoidosis, endocrine opthalmopathy, etc.);

reversible obstructive airways diseases [asthma (e.g. bronchial asthma, allergic asthma, intrinsic asthma, extrinsic asthma, dust asthma, etc.), particularly chronic or inveterate asthma (e.g. late asthma, airway hyper-responsiveness, etc.), bronchitis, etc.];

mucosal or vascular inflammations (e.g. gastric ulcer, ischemic or thrombotic vascular injury, ischemic bowel diseases, enteritis, necrotizing enterocolitis, intestinal damages associated with thermal burns, leukotriene B4-mediated diseases, etc.);

intestinal inflammations/allergies (e.g. coeliac diseases, proctitis, eosinophilic gastroenteritis, mastocytosis, Crohn's disease, ulcerative colitis, etc.);

food-related allergic diseases with symptomatic manifestation remote from the gastrointestinal tract (e.g. migraine, rhinitis, eczema, etc.);

renal diseases (e.g. intestitial nephritis, Goodpasture's syndrome, hemolytic uremic syndrome, diabetic nephropathy, etc.); nervous diseases (e.g. multiple myositis, Guillain-Barre syndrome, Meniere's disease, multiple neuritis, solitary neuritis, cerebral infarction, Alzheimer's disease, Parkinson's disease, amyotrophic lateral sclerosis (ALS), radiculopathy, etc.);

cerebral ischemic diseases (e.g., head injury, hemorrhage in brain (e.g., subarachnoid hemorrhage, intracerebral hemorrhage, etc.), cerebral thrombosis, cerebral embolism, cardiac arrest, stroke, transient ischemic attack (TIA), hypertensive encephalopathy, etc.);

endocrine diseases (e.g. hyperthyroidism, Basedow's disease, etc.);

hematic diseases (e.g. pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, etc.);

bone diseases (e.g. osteoporosis, etc.);

respiratory diseases (e.g. sarcoidosis, pulmonary fibrosis, idiopathic interstitial pneumonia, etc.);

skin diseases (e.g. dermatomyositis, leukoderma vulgaris, ichthyosis vulgaris, photosensitivity, cutaneous T-cell lymphoma, etc.);

circulatory diseases (e.g. arteriosclerosis, atherosclerosis, aortitis syndrome, polyarteritis nodosa, myocardosis, etc.);

collagen diseases (e.g. scleroderma, Wegener's granuloma, Sjögren's syndrome, etc.);

adiposis;

eosinophilic fasciitis;

periodontal diseases (e.g. damage to gingiva, periodontium, alveolar bone or substantia ossea dentis, etc.);

nephrotic syndrome (e.g. glomerulonephritis, etc.);

male pattern alopecia, alopecia senile;

muscular dystrophy;

pyoderma and Sezary syndrome;

chromosome abnormality-associated diseases (e.g. Down's syndrome, etc.);

Addison's disease;

active oxygen-mediated diseases {e.g. organ injury [e.g. ischemic circulation disorders of organs (e.g. heart, liver, kidney, digestive tract, etc.) associated with preservation, transplantation, ischemic diseases (e.g. thrombosis, cardial infarction, etc.), etc.];

intestinal diseases (e.g. endotoxin shock, pseudomembranous colitis, drug- or radiation-induced colitis, etc.);

renal diseases (e.g. ischemic acute renal insufficiency, chronic renal failure, etc.);

pulmonary diseases (e.g. toxicosis caused by pulmonary oxygen or drugs (e.g. paracort, bleomycin, etc.), lung cancer, pulmonary emphysema, etc.);

ocular diseases (e.g. cataracta, iron-storage disease (siderosis bulbi), retinitis, pigmentosa, senile plaques, vitreous scarring, corneal alkali burn, etc.);

dermatitis (e.g. erythema multiforme, linear immunoglobulin A bullous dermatitis, cement dermatitis, etc.); and other diseases (e.g. gingivitis, periodontitis, sepsis, pancreatitis, diseases caused by environmental pollution (e.g. air pollution, etc.), aging, carcinogen, metastasis of carcinoma, hypobaropathy, etc.)};

diseases caused by histamine release or leukotriene C4 release; restenosis of coronary artery following angioplasty and prevention of postsurgical adhesions;

autoimmune diseases and inflammatory conditions (e.g., primary mucosal edema, autoimmune atrophic gastritis, premature menopause, male sterility, juvenile diabetes mellitus, pemphigus vulgaris, pemphigoid, sympathetic ophthalmitis, lens-induced uveitis, idiopathic leukopenia, active chronic hepatitis, idiopathic cirrhosis, discoid lupus erythematosus, autoimmune orchitis, arthritis (e.g. arthritis deformans, etc.), polychondritis, etc.);

Human Immunodeficiency Virus (HIV) infection, AIDS; allergic conjunctivitis;

hypertrophic cicatrix, keloid due to trauma, burn or surgery, vascular intimal hyperplasia, etc.

Furthermore, as an antiproliferative agent, HDAC inhibitor may have potential in the treatment of coronary artery disease, particularly in preventing restenosis in patients undergoing percutaneous transluminal coronary angiography (PTCA).

Therefore, the pharmaceutical composition of the present invention is useful for the therapy and prophylaxis of liver diseases [e.g. immunogenic diseases (e.g. chronic autoimmune liver diseases such as autoimmune hepatic diseases, primary biliary cirrhosis, sclerosing cholangitis, etc.), partial liver resection, acute liver necrosis (e.g. necrosis caused by toxins, viral hepatitis, shock, anoxia, etc.), hepatitis B, non-A non-B hepatitis, hepatocirrhosis, hepatic failure (e.g. fulminant, hepatitis, late-onset hepatitis, "acute-on-chronic" liver failure (acute liver failure on chronic liver diseases, etc.), etc.), etc.].

The pharmaceutical composition of the present invention can be used in the form of pharmaceutical preparation, for example, in a solid, semisolid or liquid form, which contains the histone deacetylase inhibitor, such as the compound (I), as an active ingredient in admixture with an organic or inorganic carrier or excipient suitable for external, enteral or parenteral administrations. The active ingredient may be compounded, for example, with the usual non-toxic, pharmaceutically acceptable carriers for tablets, pellets, capsules, suppositories, solutions, emulsions, suspensions, injections, ointments, liniments, eye drops, lotion, gel, cream, and any other form suitable for use.

The carriers those can be used for the present invention include water, glucose, lactose, gum acacia, gelatin, mannitol, starch paste, magnesium trisilicate, talc, corn starch, keratin, colloidal silica, potato starch, urea and other carriers suitable for use in manufacturing preparations in a solid, semisolid, or liquid form. Furthermore, auxiliary, stabilizing, thickening, solubilizing and coloring agents and perfumes may be used.

For applying the composition to human, it is preferable to apply it by intravenous, intramuscular, topical or oral administration, or by a vascular stent impregnated with the compound (I). While the dosage of therapeutically effective amount of the histone deacetylase inhibitor, such as the compound (I), varies from and also depends upon the age and condition of each individual patient to be treated, when an individual patient is to be treated, in the case of intravenous administration, a daily dose of 0.01-10 mg of the histone deacetylase inhibitor, such as the compound (I), per kg weight of human being, in the case of intramuscular administration, a daily dose of 0.1-10 mg of the histone deacetylase inhibitor, such as the compound of the formula (I), per kg weight of human being, and in the case of oral administration, a daily dose of 0.5-50 mg of the histone deacetylase inhibitor, such as the compound (I), per kg weight of human being, is generally given for treatment.

During the preparation of the above-mentioned pharmaceutical administration forms, the compound (I) or a salt thereof can also be combined together with other immunosuppressive substances, for example rapamycin, mycophenolic acid, cyclosporin A, tacrolimus or brequinar sodium.

Hereinafter the reactions in each Preparations and Examples for preparing the compound (I) of the present invention are explained in more detail. The invention should not be restricted by the following Preparations and Examples in any way.

Preparation 1

To a (3-fluorophenyl)acetic acide (5 g) and N,O-dimethylhydroxylamine hydrochloride (3.48 g) and HOBT (4.82 g) and WSCD-HCl (6.84 g) in DMF (50 mL) was added $Et_3N$ (9.5 mL). The mixture was stirred for 16 hours, was added water and extracted with AcOEt. The organic layer was washed with water and dried over $MgSO_4$, evaporated in vacuo to give 2-(3-fluorophenyl)-N-methoxy-N-methylacetamide (3.92 g) as an oil.

ESI-MS; 198 (M+H)+

The following compounds were obtained in a similar manner to that of Preparation 1.

Preparation 2

2-(2-fluorophenyl)-N-methoxy-N-methylacetamide

ESI-MS; 198 (M+H)+

Preparation 3

2-(2,4-difluorophenyl)-N-methoxy-N-methylacetamide

ESI-MS; 216 (M+H)+

Preparation 4

2-(2,6-difluorophenyl)-N-methoxy-N-methylacetamide

ESI-MS; 216 (M+H)+

Preparation 5

N-methoxy-N-methyl-2-(2-thienyl)acetamide

ESI-MS; 186 (M+H)+

Preparation 6

2-(3,4-difluorophenyl)-N-methoxy-N-methylacetamide $^1$H-NMR (DMSO-$d_6$, δ): 3.11 (3H, s), 3.70 (3H, s), 3.76 (2H, s), 7.06-7.09 (1H, m), 7.27-7.38 (2H, m)

Preparation 7

To a cooled solution of 2-(3-fluorophenyl)-N-methoxy-N-methylacetamide (613 mg) in THF (10 mL) at −40° C. was added dropwise a solution of 0.99M DIBAL solution of hexane (3.14 mL) at −20° C. under nitrogen atmosphere. After stirring for 0.5 hours, 1N—HCl aq. (20 mL) was added to the reaction solution and the mixture was stirred for 5 minutes. IPE was added to the mixture. The organic layer was washed with 1N—HCl aq. (20 mL) and dried over $MgSO_4$ and evaporated in vacuo. To a solution of the residue and methyl (2E)-3-{5-[(3R)-3-pyrrolidinylamino]-2-pyrazinyl}acrylate dihydrochloride (500 mg) in $CH_2Cl_2$ (10 ml) was added NaBH(OAc)$_3$ and DIEA. The mixture was stirred for 24 hours at ambient temperature and added aq.$NaHCO_3$ and $CH_2Cl_2$. After stirring for 0.5 hours, the organic layer was evaporated in vacuo. The residue was chromatographed on silica gel using a mixture of $CHCl_3$-MeOH (20:1). The desired fractions were collected and evaporated in vacuo to give methyl (2E)-3-[5-({(3R)-1-[2-(3-fluorophenyl)ethyl]-3-pyrrolidinyl}amino)-2-pyrazinyl]acrylate (242 mg) as a solid.

ESI-MS; 371 (M+H)+

The following compounds were obtained in a similar manner to that of Preparation 7.

Preparation 8

Methyl (2E)-3-[5-({(3R)-1-[2-(2,4-difluorophenyl)ethyl]-3-pyrrolidinyl}amino)-2-pyrazinyl]acrylate

ESI-MS; 389 (M+H)+

Preparation 9

Methyl(2E)-3-[5-({(3R)-1-[2-(2,6-difluorophenyl)ethyl]-3-pyrrolidinyl}amino)-2-pyrazinyl]acrylate

ESI-MS; 389 (M+H)+

Preparation 10

Methyl (2E)-3-[5-({(3R)-1-[2-(2-thienyl)ethyl]-3-pyrrolidinyl}amino)-2-pyrazinyl]acrylate

ESI-MS; 359 (M+H)+

Preparation 11

Methyl (2E)-3-[5-({(3R)-1-[2-(3,4-difluorophenyl)ethyl]-3-pyrrolidinyl}amino)-2-pyrazinyl]acrylate

ESI-MS; 389 (M+H)+

Preparation 12

Methyl (2E)-3-[5-({(3R)-1-[2-(3-fluorophenyl)ethyl]-3-piperidinyl}amino)-2-pyrazinyl]acrylate

ESI-MS; 385 (M+H)+

Preparation 13

Methyl (2E)-3-[5-({(3R)-1-[2-(2-fluorophenyl)ethyl]-3-piperidinyl}amino)-2-pyrazinyl]acrylate

ESI-MS; 385 (M+H)+

Preparation 14

Methyl (2E)-3-[5-({(3R)-1-[2-(2,4-difluorophenyl)ethyl]-3-piperidinyl}amino)-2-pyrazinyl]acrylate

ESI-MS; 403 (M+H)+

Preparation 15

Methyl (2E)-3-[5-({(3R)-1-[2-(3,4-difluorophenyl)ethyl]-3-piperidinyl}amino)-2-pyrazinyl]acrylate

ESI-MS; 403 (M+H)+

Preparation 16

A mixture of methyl (2E)-3-[5-({(3R)-1-[2-(3-fluorophenyl)ethyl]-3-pyrrolidinyl}amino)-2-pyrazinyl]acrylate (235 mg) and 1N—NaOH aq. (1.3 mL) in MeOH (4.7 mL) was heated at 50° C. for 3 hours. After cooling, 1N—HCl (1.37 mL) was added to the solution. The mixture was evaporated and azeotroped with dioxane and toluene to give a crude (2E)-3-[5-({(3R)-1-[2-(3-fluorophenyl)ethyl]-3-pyrrolidinyl}amino)-2-pyrazinyl]acrylic acid (226 mg).

ESI-MS; 357 (M+H)+

The following compounds were obtained in a similar manner to that of Preparation 16.

Preparation 17

(2E)-3-[5-({(3R)-1-[2-(2,4-difluorophenyl)ethyl]-3-pyrrolidinyl}amino)-2-pyrazinyl]acrylic acid

ESI-MS; 375 (M+H)+

Preparation 18

(2E)-3-[5-({(3R)-1-[2-(2,6-difluorophenyl)ethyl]-3-pyrrolidinyl}amino)-2-pyrazinyl]acrylic acid

ESI-MS; 375 (M+H)+

Preparation 19

(2E)-3-[5-({(3R)-1-[2-(2-thienyl)ethyl]-3-pyrrolidinyl}amino)-2-pyrazinyl]acrylic acid

ESI-MS; 345 (M+H)+

Preparation 20

(2E)-3-[5-({(3R)-1-[2-(3,4-difluorophenyl)ethyl]-3-pyrrolidinyl}amino)-2-pyrazinyl]acrylic acid

ESI-MS; 375 (M+H)+

Preparation 21

(2E)-3-[5-({(3R)-1-[2-(3-fluorophenyl)ethyl]-3-piperidinyl}amino)-2-pyrazinyl]acrylic acid

ESI-MS; 371 (M+H)+

Preparation 22

(2E)-3-[5-({(3R)-1-[2-(2-fluorophenyl)ethyl]-3-piperidinyl}amino)-2-pyrazinyl]acrylic acid

ESI-MS; 371 (M+H)+

Preparation 23

(2E)-3-[5-({(3R)-1-[2-(2,4-difluorophenyl)ethyl]-3-piperidinyl}amino)-2-pyrazinyl]acrylic acid

ESI-MS; 389 (M+H)+

Preparation 24

(2E)-3-[5-({(3R)-1-[2-(3,4-difluorophenyl)ethyl]-3-piperidinyl}amino)-2-pyrazinyl]acrylic acid

ESI-MS; 389 (M+H)+

Preparation 25

A mixture of (2E)-3-[5-({(3R)-1-[2-(3-fluorophenyl)ethyl]-3-pyrrolidinyl}amino)-2-pyrazinyl]acrylic acid (226 mg) and 2-(aminooxy)tetrahydro-2H-pyran and WSCD-HCl was stirred for 24 hours at ambient temperature. $CH_2Cl_2$ was added the mixture. The $CH_2Cl_2$ layer was washed with water and evaporated in vacuo. The residue was chromatographed on silica gel using a mixture of $CHCl_3$-MeOH (10:1) to give (2E)-3-[5-({(3R)-1-[2-(3-fluorophenyl)ethyl]-3-pyrrolidinyl}amino)-2-pyrazinyl]-N-(tetrahydro-2H-pyran-2-yloxy)acrylamide (160 mg) as a solid.

ESI-MS; 456 (M+H)+

The following compounds were obtained in a similar manner to that of Preparation 25.

Preparation 26

(2E)-3-[5-({(3R)-1-[2-(2,4-difluorophenyl)ethyl]-3-pyrrolidinyl}amino)-2-pyrazinyl]-N-(tetrahydro-2H-pyran-2-yloxy)acrylamide

ESI-MS; 474 (M+H)+

Preparation 27

(2E)-N-(tetrahydro-2H-pyran-2-yloxy)-3-[5-({(3R)-1-[2-(2-thienyl)ethyl]-3-pyrrolidinyl}amino)-2-pyrazinyl]acrylamide

ESI-MS; 444 (M+H)+

Preparation 28

(2E)-3-[5-({(3R)-1-[2-(2,6-difluorophenyl)ethyl]-3-pyrrolidinyl}amino)-2-pyrazinyl]-N-(tetrahydro-2H-pyran-2-yloxy)acrylamide

ESI-MS; 474 (M+H)+

Preparation 29

(2E)-3-[5-({(3R)-1-[2-(3,4-difluorophenyl)ethyl]-3-pyrrolidinyl}amino)-2-pyrazinyl]-N-(tetrahydro-2H-pyran-2-yloxy)acrylamide

ESI-MS; 474 (M+H)+

Preparation 30

(2E)-3-[5-({(3R)-1-[2-(3-fluorophenyl)ethyl]-3-piperidinyl}amino)-2-pyrazinyl]-N-(tetrahydro-2H-pyran-2-yloxy)acrylamide

ESI-MS; 470 (M+H)+

Preparation 31

(2E)-3-[5-({(3R)-1-[2-(2-fluorophenyl)ethyl]-3-piperidinyl}amino)-2-pyrazinyl]-N-(tetrahydro-2H-pyran-2-yloxy)acrylamide

ESI-MS; 470 (M+H)+

Preparation 32

(2E)-3-[5-({(3R)-1-[2-(2,4-difluorophenyl)ethyl]-3-piperidinyl}amino)-2-pyrazinyl]-N-(tetrahydro-2H-pyran-2-yloxy)acrylamide

ESI-MS; 488 (M+H)+

Preparation 33

(2E)-3-[5-({(3R)-1-[2-(3,4-difluorophenyl)ethyl]-3-piperidinyl}amino)-2-pyrazinyl]-N-(tetrahydro-2H-pyran-2-yloxy)acrylamide

ESI-MS; 488 (M+H)+

Preparation 34

To a suspension of methyl (2E)-3-{5-[(3R)-3-pyrrolidinylamino]-2-pyrazinyl}acrylate dihydrochloride (240 mg) in CH$_2$Cl$_2$ (2.4 mL) was added DIEA (260 uL), 2-(dimethylamino) benzaldehyde (122.6 mg), and sodium triacetoxyborohydride (317 mg), which was stirred at room temperature for 15 hours. To the resultant was added saturated NaHCO$_3$ aq., which was stirred for 20 min. The mixture was extracted with CH$_2$Cl$_2$. The organic phase was washed with brine and dried over Na$_2$SO$_4$, filtered, and evaporated in vacuo. The residue was washed with hexane to give methyl (2E)-3-[5-({(3R)-1-[2-(dimethylamino)benzyl]-3-pyrrolidinyl}amino)-2-pyrazinyl]acrylate as a beige powder.

ESI-MS; 382 (M+H)+

The following compounds were obtained in a similar manner to that of Preparation 34.

Preparation 35

Methyl (2E)-3-(5-{[(3R)-1-(4-fluoro-3-methoxybenzyl)-3-pyrrolidinyl]amino}-2-pyrazinyl)acrylate

ESI-MS; 387 (M+H)+

Preparation 36

Methyl (2E)-3-(5-{[(3R)-1-(cyclopentylmethyl)-3-pyrrolidinyl]amino}-2-pyrazinyl)acrylate

ESI-MS; 331 (M+H)+

Preparation 37

Methyl (2E)-3-(5-{[(3R)-1-{[1-(hydroxymethyl)cyclohexyl]methyl}-3-pyrrolidinyl]amino}-2-pyrazinyl)acrylate

ESI-MS; 375 (M+H)+

Preparation 38

Methyl (2E)-3-(5-{[(3R)-1-(5-fluoro-2-methoxybenzyl)-3-pyrrolidinyl]amino}-2-pyrazinyl)acrylate

ESI-MS; 387 (M+H)+

Preparation 39

To a solution of methyl (2E)-3-[5-({(3R)-1-[2-(dimethylamino) benzyl]-3-pyrrolidinyl}amino)-2-pyrazinyl]acrylate (235 mg) in MeOH (1.9 mL) was added 1N NaOH aq. (1.2 mL), which was stirred at 55° C. for 1 hour. To the reaction mixture was added 1N—HCl aq. (1.2 mL), and evaporated in vacuo to give a crude (2E)-3-[5-({(3R)-1-[2-(dimethylamino)benzyl]-3-pyrrolidinyl}amino)-2-pyrazinyl]acrylic acid as, a brown solid (0.310 mg). This was used next reaction without purification.

ESI-MS; 368 (M+H)+

The following compounds were obtained in a similar manner to that of Preparation 39.

Preparation 40

(2E)-3-(5-{[(3R)-1-(4-fluoro-3-methoxybenzyl)-3-pyrrolidinyl]amino}-2-pyrazinyl)acrylic acid

ESI-MS; 373 (M+H)+

Preparation 41

(2E)-3-(5-{[(3R)-1-(cyclopentylmethyl)-3-pyrrolidinyl]amino}-2-pyrazinyl)acrylic acid

ESI-MS; 317 (M+H)+

Preparation 42

(2E)-3-(5-{[(3R)-1-{[1-(hydroxymethyl)cyclohexyl]methyl}-3-pyrrolidinyl]amino}-2-pyrazinyl)acrylic acid

ESI-MS; 361 (M+H)+

Preparation 43

(2E)-3-(5-{[(3R)-1-(7-oxabicyclo[2.2.1]hept-1-ylmethyl)-3-pyrrolidinyl]amino}-2-pyrazinyl)acrylic acid

ESI-MS; 345 (M+H)+

Preparation 44

(2E)-3-(5-{[(3R)-1-(5-fluoro-2-methoxybenzyl)-3-pyrrolidinyl]amino}-2-pyrazinyl)acrylic acid

ESI-MS; 373 (M+H)+

Preparation 45

To a mixture of crude (2E)-3-[5-({(3R)-1-[2-(dimethylamino) benzyl]-3-pyrrolidinyl}amino)-2-pyrazinyl]acrylic acid (311 mg), O-(tetrahydro-2H-pyran-2-yl)hydroxylamine (108 mg), and HOBT (125 mg) in DMF (2.4 mL) was added WSCD (164 uL), which was stirred at room temperature for 17 hours. To the resultant was added saturated $NaHCO_3$ aq. The mixture was extracted with AcOEt. The organic phase was washed with brine, dried over $Na_2SO_4$, filtered, and evaporated in vacuo. The residue was purified by column chromatography on silica gel to give (2E)-3-[5-({(3R)-1-[2-(dimethylamino)benzyl]-3-pyrrolidinyl}amino)-2-pyrazinyl]-N-(tetrahydro-2H-pyran-2-yloxy)acrylamide (195 mg) as a yellow amorphous.

ESI-MS; 467 (M+H)+

The following compounds were obtained in a similar manner to that of Preparation 45.

Preparation 46

(2E)-3-(5-{[(3R)-1-(4-fluoro-3-methoxybenzyl)-3-pyrrolidinyl]amino}-2-pyrazinyl)-N-(tetrahydro-2H-pyran-2-yloxy)acrylamide

ESI-MS; 472 (M+H)+

Preparation 47

(2E)-3-(5-{[(3R)-1-(cyclopentylmethyl)-3-pyrrolidinyl]amino}-2-pyrazinyl)-N-(tetrahydro-2H-pyran-2-yloxy)acrylamide

ESI-MS; 416 (M+H)+

Preparation 48

(2E)-3-(5-{[(3R)-1-{[1-(hydroxymethyl)cyclohexyl]methyl}-3-pyrrolidinyl]amino}-2-pyrazinyl)-N-(tetrahydro-2H-pyran-2-yloxy)acrylamide

ESI-MS; 460 (M+H)+

Preparation 49

(2E)-3-(5-{[(3R)-1-(7-oxabicyclo[2.2.1]hept-1-ylmethyl)-3-pyrrolidinyl]amino}-2-pyrazinyl)-N-(tetrahydro-2H-pyran-2-yloxy)acrylamide

ESI-MS; 444 (M+H)+

Preparation 50

(2E)-3-(5-{[(3R)-1-(5-fluoro-2-methoxybenzyl)-3-pyrrolidinyl]amino}-2-pyrazinyl)-N-(tetrahydro-2H-pyran-2-yloxy)acrylamide

ESI-MS; 472 (M+H)+

Preparation 51

To a solution of tert-butyl [(3R)-1-(7-oxabicyclo[2.2.1]hept-1-ylmethyl)-3-pyrrolidinyl]carbamate (377 mg) in AcOEt (3.8 mL) was added 4N HCl—AcOEt (3.2 mL), which was stirred at room temperature for 5 hours. The solvent was evaporated. The residue was dried to give (3R)-1-(7-oxabicyclo[2.2.1]hept-1-ylmethyl)-3-pyrrolidinamine dihydrochloride (370 mg) as an orange amorphous.

ESI-MS; 197 (M+H)+

Preparation 52

To a mixture of ethyl (2E)-3-(5-chloropyrazin-2-yl)acrylate (242.8 mg) in DMA (1.9 mL) was added (3R)-1-(7-oxabicyclo[2.2.1]hept-1-ylmethyl)pyrrolidin-3-amine dihydrochloride (370 mg) and $Et_3N$ (796 uL), which was stirred at 100° C. for 24 hours. To the resultant was added $H_2O$, which was extracted with AcOEt. The organic phase was washed with brine, dried over $Na_2SO_4$, filtered, and evaporated in vacuo. The residue was purified by column chromatography on silica gel to give ethyl (2E)-3-(5-{[(3R)-1-(7-oxabicyclo[2.2.1]hept-1-ylmethyl)-3-pyrrolidinyl]amino}-2-pyrazinyl)acrylate (425 mg) as a brown solid.

ESI-MS; 373 (M+H)+

Preparation 53

To a solution of 4-methylenecyclohexanol (1.88 g) in $CH_2Cl_2$ (37.6 mL) was added N-iodosuccinimide (4.5 g) under nitrogen atmosphere, which was stirred at ambient temperature for 3 hours. The resultant was washed with $Na_2S_2O_3$ aq., $H_2O$, and brine. The organic phase was dried over $Na_2SO_4$, filtered, and evaporated in vacuo. The residue was purified by column chromatography on silica gel to give 1-(iodomethyl)-7-oxabicyclo[2.2.1]heptane (1.5 g) as colorless oil.

$^1$H-NMR ($CDCl_3$, δ): 1.60-1.81 (6H, m), 1.85-1.97 (2H, m), 3.55 (2H, s), 4.65 (1H, t, J=5.2 Hz).

Preparation 54

The mixture of tert-butyl (3R)-3-pyrrolidinylcarbamate (500 mg), 1-(iodomethyl)-7-oxabicyclo[2.2.1]heptane (639 mg) and $K_2CO_3$ (742 mg) in DMF (5 mL) was stirred at 75° C. for 32 hours. The resultant was added $H_2O$, extracted with AcOEt. The organic phase was washed with brine, dried over $Na_2SO_4$, filtered, and evaporated in vacuo. The residue was purified by column chromatography on silica gel to give tert-butyl [(3R)-1-(7-oxabicyclo[2.2.1]hept-1-ylmethyl)-3-pyrrolidinyl]carbamate (416 mg) as orange oil.

ESI-MS; 297 (M+H)+

Preparation 55

A mixture of 1-naphthaldehyde (143 µl), methyl (2E)-3-{5-[(3R)-3-pyrrolidinylamino]-2-pyrazinyl}acrylate dihydrochloride (260 mg) and DIEA (282 µl) in dichloromethane (20 mL) was stirred at ambient temperature for 1 hour. After then, sodium triacetoxyborohydride (515 mg) was added and stirred overnight. Water and chloroform was added to the reaction mixture, and organic layer was separated. Aqueous layer was extracted twice with chloroform and combined organic layer was washed twice with water, dried over magnesium sulfate, filtered and evaporated. The residue was purified by column chromatography on silica gel to give methyl (2E)-3-(5-{[(3R)-1-(1-naphthylmethyl)-3-pyrrolidinyl]amino}-2-pyrazinyl)acrylate (480 mg).

ESI-MS; 389 (M+H)+.

$^1$H-NMR (CDCl$_3$, δ): δ 1.65-1.75 (1H, m), 2.32-2.51 (2H, m), 2.68-2.78 (2H, m), 2.98 (1H, dt, J=4, 8.7 Hz), 3.79 (3H, s), 4.05 (1H, d, J=13 Hz), 4.12 (1H, d, J=13 Hz), 4.44-4.52 (1H, m), 5.27 (1H, d, J=7.2 Hz), 6.67 (1H, d, J=15.8 Hz), 7.39-7.58 (5H, m), 7.56 (1H, d, J=15.8 Hz), 7.77-7.9 (2H, m), 7.82 (1H, d, J=1.4 Hz), 8.02 (1H, d, J=1.4 Hz), 8.26 (1H, d, J=8 Hz).

The following compounds were obtained in a similar manner to that of Preparation 55.

Preparation 56

Methyl (2E)-3-[5-({(3R)-1-[2-(1-naphthyl)ethyl]-3-pyrrolidinyl}amino)-2-pyrazinyl]acrylate

ESI-MS; 403 (M+H)+.

$^1$H-NMR (CDCl$_3$, δ): 1.72-1.82 (1H, m), 2.37-2.50 (2H, m), 2.71-2.77 (1H, m), 2.81-2.93 (2H, m), 3.08-3.14 (1H, m), 3.31 (2H, t, J=8.2 Hz), 3.80 (3H, s), 4.48-4.56 (1H, m), 5.35 (1H, d, J=7.6 Hz), 6.70 (1H, d, J=15.5 Hz), 7.36-7.42 (2H, m), 7.46-7.54 (2H, m), 7.59 (1H, d, J=15.5 Hz), 7.73 (1H, d, J=8.0 Hz), 7.86 (1H, dd, J=7.8 and 1.6 Hz), 7.89 (1H, d, J=1.2 Hz), 8.04-8.07 (1H, m), 8.06 (1H, d, J=1.2 Hz).

Preparation 57

(2E)-3-(5-{[(3R)-1-(1-naphthylmethyl)-3-pyrrolidinyl]amino}-2-pyrazinyl)-N-(tetrahydro-2H-pyran-2-yloxy)acrylamide $^1$H-NMR (CDCl$_3$, δ): δ1.50-1.94 (7H, m), 2.34-2.6 (2H, m), 2.75-2.85 (2H, m), 3-3.13 (2H, m), 3.61-3.7 (1H, m), 3.96 (1H, t, J=8.2 Hz), 4.12 (1H, d, J=12.9 Hz), 4.19 (1H, d, J=12.9 Hz), 4.48-4.57 (1H, m), 5.99 (1H, br.s), 7.4-7.64 (6H, m), 7.81 (1H, d, J=8.8 Hz), 7.82 (1H, s), 7.88 (1H, d, J=8.8 Hz), 8 (1H, s), 8.25 (1H, d, J=8.6 Hz).

ESI-MS; 474 (M+H)+.

Preparation 58

A mixture of methyl (2E)-3-(5-chloro-2-pyrazinyl)acrylate (10.00 g), tert-butyl (3R)-3-amino-1-pyrrolidinecarboxylate (14.01 g) and potassium phosphate (21.30 g) in DMA (25 mL) was stirred at 90-95° C. for 6 hours under nitrogen atmosphere. After addition of water, the reaction mixture was extracted with AcOEt. Water was added to the organic layer and the mixture was adjusted to pH 8 with 1N HCl aq., washed with water, dried over magnesium sulfate and concentrated under reduced pressure to give a residue. The residue was purified by silica gel (chromatorex NH) (hexane-AcOEt 60:40 v/v) to give tert-butyl (3R)-3-({5-[(1E)-3-methoxy-3-oxo-1-propen-1-yl]-2-pyrazinyl}amino)-1-pyrrolidinecarboxylate as a solid (10.64 g).

m.p.: 138-140° C.

IR (KBr): 3319, 1718, 1676, 1635, 1591, 1525 cm-1

ESI-MS; 719 (2M+Na)+, 371 (M+Na)+

$^1$H-NMR (DMSO-d$_6$, δ): 1.47 (9H, s), 3.80 (3H, s), 6.71 (1H, d), 7.59 (1H, d), 7.95 (1H, s), 8.08 (1H, s)

The following compound was obtained in a similar manner to that of Preparation 58.

Preparation 59 tert-Butyl (3R)-3-({5-[(1E)-3-methoxy-3-oxo-1-propen-1-yl]-2-pyrazinyl}amino)-1-piperidinecarboxylate m.p.: 153-155° C.

IR (KBr): 3342, 1695, 1631, 1593, 1531 cm-1

ESI-MS; 747 (2M+Na)+, 385 (M+Na)+

ESI-MS; 361 (M−H)−

$^1$H-NMR (DMSO-d$_6$, δ): 3.70 (3H, s), 6.53 (1H, d, J=15.49 Hz), 7.58 (1H, d, J=15.49 Hz), 7.71 (1H, d, J=6.86 Hz), 8.04 (1H, s), 8.25 (1H, s)

Preparation 60

Under ice-cooling, N,O-dimethylhydroxylamine hydrochloride (3.42 g) was added to a mixture of (2-chlorophenyl)acetic acid (3.41 g) and WSCD (2.05 g) in dichloromethane (30 mL). The mixture was stirred at 0-10° C. for an hour and at 20-25° C. for 20 hours, washed with water, dried over magnesium sulfate and concentrated under reduced pressure to give a residue. The residue was purified by silica gel (chromatorex NH) (hexane-AcOEt 50:50 v/v) to give 2-(2-chlorophenyl)-N-methoxy-N-methylacetamide as oil (3.99 g).

ESI-MS; 238 and 236 (M+Na)+, 216 and 214 (M+H)+

$^1$H-NMR (CDCl$_3$, δ): 3.23 (3H, s), 3.70 (3H, s), 3.92 (2H, s), 7.18-7.41 (4H, m)

The following compounds were obtained in a similar manner to that of Preparation 60.

Preparation 61

N-methoxy-2-(4-methoxyphenyl)-N-methylacetamide

ESI-MS; 232 (M+Na)+, 210 (M+H)+

$^1$H-NMR (CDCl$_3$, δ): 3.19 (3H, s), 3.62 (3H, s), 3.71 (2H, s), 3.79 (3H, s), 6.82-6.88 (2H, m), 7.18-7.25 (2H, m)

Preparation 62

2-(4-chlorophenyl)-N-methoxy-N-methylacetamide m.p.: 47-49° C.

IR (KBr): 1672 cm-1

ESI-MS; 238 and 236 (M+Na)+, 216 and 214 (M+H)+

$^1$H-NMR (CDCl$_3$, δ): 3.19 (3H, s), 3.63 (3H, s), 3.74 (2H, s), 7.09-7.31 (4H, m)

Preparation 63

2-(4-bromophenyl)-N-methoxy-N-methylacetamide m.p.: 64-66° C.
IR (KBr): 1670 cm-1
ESI-MS; 282 and 280 (M+Na)+, 260 and 258 (M+H)+
$^1$H-NMR (CDCl$_3$, δ): 3.19 (3H, s), 3.63 (3H, s), 3.72 (2H, s), 7.14-7.22 (2H, m), 7.40-7.47 (2H, m)

Preparation 64

To a suspension of (R)-3-Boc-aminopiperidine (1.01 g), 3-phenylpropanal (817 mg) and DIEA (1.31 g) in CH$_2$Cl$_2$ (5 mL) was added sodium triacetoxyborohydride (2.15 g), and the reaction mixture was stirred at ambient temperature for 5 hours. To the resultant was added saturated aq.NaHCO$_3$ (15 ml). After stirring for 30 min, the mixture was extracted with CH$_2$Cl$_2$. The organic phase was washed with water and dried over MgSO$_4$, filtered, and evaporated in vacuo. The residue was column chromatographed on silica gel to give tert-butyl [(3R)-1-(3-phenylpropyl)-3-piperidinyl] carbamate (1.47 g) as a white crystal.

m.p.: 73-74.5° C.
IR (KBr): 3361, 1684, 1531 cm-1
ESI-MS; 341 (M+Na)+, 319 (M+H)+
$^1$H-NMR (CDCl$_3$, δ): 1.49 (9H, s), 7.14-7.33 (5H, m)

Preparation 65

To a solution of (3R)-3-({5-[(1E)-3-methoxy-3-oxo-1-propen-1-yl]-2-pyrazinyl}amino)-1-pyrrolidinecarboxylate (10.50 g) in 1,2-dichloroethane (100 mL) was added a 4N HCl in dioxane (100 mL) and the mixture was stirred at 20-25° C. for 2 hours under nitrogen atmosphere to give a solid. The solid was collected by filtration to give methyl (2E)-3-{5-[(3R)-3-pyrrolidinylamino]-2-pyrazinyl}acrylate dihydrochloride (9.73 g).

ESI-MS; 249 (M+H)+
$^1$H-NMR (DMSO-d$_6$, δ): 1.92-2.06 (1H, m), 2.05-2.29 (1H, m), 3.06-3.50 (4H, m), 3.71 (3H, s), 4.43-4.52 (1H, m), 6.57 (1H, d, J=15.53 Hz), 7.60 (1H, d, J=15.53 Hz), 8.11 (1H, s), 8.29 (1H, s), 8.47 (1H, br.s), 9.59 (1H, br.s)

The following compound was obtained in a similar manner to that of Preparation 65.

Preparation 66

Methyl (2E)-3-{5-[(3R)-3-piperidinylamino]-2-pyrazinyl}acrylate dihydrochloride

ESI-MS; 263 (M+H)+
$^1$H-NMR (DMSO-d$_6$, δ) 1.50-1.96 (4H, m), 2.70-3.60 (4H, m), 3.71 (3H, s), 4.10-4.25 (1H, m), 6.56 (1H, d, J=15.53 Hz), 7.60 (1H, d, J=15.53 Hz), 8.10 (1H, s), 8.20 (1H, br.s), 8.28 (1H, s), 9.35 (1H, br.s)

Preparation 67

To a solution of tert-butyl [(3R)-1-(3-phenylpropyl)-3-piperidinyl]carbamate (880 mg) in AcOEt (1.3 mL) was added 4N HCl—AcOEt (8.8 mL). The mixture was stirred at ambient temperature for 3 hours. The solvent was evaporated. Dichloromethane (10 ml) and saturated sodium bicarbonate (15 ml) was added. Aqueous layer was separated and extracted with dichloromethane. Combined organic layer was dried over magnesium sulfate, filtered and evaporated in vacuo to give (3R)-1-(3-phenylpropyl)-3-piperidineamine (586 mg) as an yellow oil.

ESI-MS; 241 (M+Na)+, 219 (M+H)+
$^1$H-NMR (CDCl$_3$, δ): 1.05-2.90 (15H, m), 7.02-7.32 (5H, m)

Preparation 68

To a mixture of methyl (2E)-3-(5-chloropyrazin-2-yl)acrylate (300 mg) in DMA (1.9 mL) was added (3R)-1-(3-phenylpropyl)-3-piperidinamine (495 mg) and potassium phosphate (642 mg). The reaction mixture was stirred at 90-95° C. for 2 hours. To the resultant was added H$_2$O (7.5 ml), and pH was adjusted to 8.0 by 1N HCl aq., and the mixture was extracted twice with AcOEt (3 ml, twice). The organic layer was dried over magnesium sulfate, filtered, and evaporated in vacuo. The residue was purified by column chromatography on silica gel and purified fractions were evaporated. Acetone and IPE was added to the residue. The resulting solid was collected by filtration to give methyl (2E)-3-[5-[{(3R)-1-(3-phenylpropyl)-3-piperidinyl}amino]-2-pyrazinyl] acrylate (202 mg) as a pale yellow solid.

m.p.: 122-123.5° C.
IR (KBr): 3230, 2939, 1714, 1637, 1595, 1527 cm-1
ESI-MS; 403 (M+Na)+, 381 (M+H)+
$^1$H-NMR (CDCl$_3$, δ): 1.50-2.70 (14H, m), 3.79 (3H, s), 4.10-4.20 (1H, m), 5.60 (1H, br.s), 6.68 (1H, d, J=15.54 Hz), 7.14-7.34 (5H, m), 7.58 (1H, d, J=15.54 Hz), 7.92 (1H, s), 8.04 (1H, s)

Preparation 69

To a suspension of methyl (2E)-3-{5-[(3R)-3-pyrrolidinylamino]-2-pyrazinyl}acrylate (335 mg) in dichloromethane (5 mL) was added DIEA (870 uL), 3-phenylpropanal (157 ul), and sodium triacetoxyborohydride (424 mg), and the reaction mixture was stirred at ambient temperature for 2 hours. To the resultant was added saturated aq.NaHCO$_3$, which was stirred for 30 min. The mixture was extracted with dichloromethane. The organic phase was washed with brine and dried over MgSO$_4$, filtered, and evaporated in vacuo. The residue was crystallized from acetone and IPE to give methyl (2E)-3-[5-[{(3R)-1-(3-phenylpropyl)-3-piperidinyl}amino]-2-pyrazinyl]acrylate (183 mg) as a pale yellow crystal. The filtrate was evaporated and the residue was column chromatographed on silica gel (hexane:AcOEt=25:75) to give 84 mg of product.

m.p.: 122-123.5° C.
IR (KBr): 3230, 2939, 1714, 1637, 1595, 1527 cm-1
ESI-MS; 403 (M+Na)+, 381 (M+H)+
$^1$H-NMR (CDCl$_3$, δ): 1.50-2.70 (14H, m), 3.79 (3H, s), 4.10-4.20 (1H, m), 5.60 (1H, br.s), 6.68 (1H, d, J=15.54 Hz), 7.14-7.34 (5H, m), 7.58 (1H, d, J=15.54 Hz), 7.92 (1H, s), 8.04 (1H, s)

Preparation 70

To a solution of methyl (2E)-3-[5-[{(3R)-1-(3-phenylpropyl)-3-piperidinyl}amino]-2-pyrazinyl] acrylate (365 mg) in MeOH (7.2 mL) was added aqueous 1N NaOH aq. (2.4 mL), and the reaction mixture was stirred at 50-55° C. for 3 hours. 1N HCl aq. (1.5 mL) was added to the mixture, and the mixture was evaporated in vacuo and co-evaporated with dioxane, dioxane-toluene, and toluene to give a crude (2E)-3-[5-{(3R)-1-(3-phenylpropyl)-3-piperidinyl}amino-2-pyrazinyl]acrylic acid as a yellow solid (365 mg).

ESI-MS; 367 (M+H)+

¹H-NMR (DMSO-d₆, δ): 6.45 (1H, d, J=15.50 Hz), 7.13-7.28 (5H, m), 7.47 (1H, d, J=15.50 Hz), 7.63 (1H, d, J=7.60 Hz), 8.03 (1H, s), 8.18 (1H, s)

The following compounds were obtained in a similar manner to that of Preparation 70.

Preparation 71

(2E)-3-[5-({(3R)-1-[2-(2-chlorophenyl)ethyl]-3-pyrrolidinyl}amino)-2-pyrazinyl]acrylic acid ESI-MS; 397 and 395 (M+Na)+, 375 and 373 (M+H)+

¹H-NMR (DMSO-d₆, δ): 1.60-1.72 (1H, m), 2.15-2.28 (1H, m), 2.45-2.94 (8H, m), 4.30-4.35 (1H, m), 6.46 (1H, d, J=15.44 Hz), 7.21-7.30 (2H, m), 7.36-7.42 (2H, m), 7.47 (1H, d, J=15.44 Hz), 7.94 (1H, d, J=6.40 Hz), 8.02 (1H, s), 8.19 (1H, s)

Preparation 72

(2E)-3-[5-({(3R)-1-[2-(4-chlorophenyl)ethyl]-3-pyrrolidinyl}amino)-2-pyrazinyl]acrylic acid ESI-MS; 397 and 395 (M+Na)+, 375 and 373 (M+H)+

¹H-NMR (DMSO-d₆, δ): 1.60-1.1.70 (1H, m), 2.13-2.25 (1H, m), 2.42-2.85 (8H, m), 4.25-4.37 (1H, m), 6.47 (1H, d, J=15.48 Hz), 7.22-7.35 (4H, m), 7.45 (1H, d, J=15.48 Hz), 7.95 (1H, d, J=6.48 Hz), 8.02 (1H, s), 8.17 (1H, s)

Preparation 73

(2E)-3-[5-({(3R)-1-[2-(4-methoxyphenyl)ethyl]-3-pyrrolidinyl}amino)-2-pyrazinyl]acrylic acid

ESI-MS; 369 (M+H)+

¹H-NMR (DMSO-d₆, δ): 1.60-1.70 (1H, m), 2.15-2.25 (1H, m), 2.45-2.86 (8H, m), 3.71 (3H, s), 4.28-4.35 (1H, m), 6.47 (1H, d, J=15.50 Hz), 6.81-6.85 (2H, m), 7.11-7.15 (2H, m), 7.46 (1H, d, J=15.50 Hz), 7.97 (1H, d, J=6.67 Hz), 8.02 (1H, d), 8.18 (1H, d)

Preparation 74

(2E)-3-[5-({(3R)-1-[2-(4-bromophenyl)ethyl]-3-pyrrolidinyl}amino)-2-pyrazinyl]acrylic acid ESI-MS; 441 and 439 (M+Na)+, 419 and 417 (M+H)+

¹H-NMR (DMSO-d₆, δ) 1.60-1.70 (1H, m), 2.15-2.25 (1H, m), 2.45-2.86 (8H, m), 3.71 (3H, s), 4.28-4.35 (1H, m), 6.47 (1H, d, J=15.50 Hz), 6.81-6.85 (2H, m), 7.11-7.15 (2H, m), 7.46 (1H, d, J=15.50 Hz), 7.97 (1H, d, J=6.67 Hz), 8.02 (1H, d), 8.18 (1H, d)

Preparation 75

(2E)-3-(5-{[(3R)-1-(2-cyclopentylethyl)-3-pyrrolidinyl]amino}-2-pyrazinyl)acrylic acid ESI-MS; 369 (M+K)+, 353 (M+Na)+, 331 (M+H)+

¹H-NMR (DMSO-d₆, δ): 6.46 (1H, d, J=15.48 Hz), 7.44 (1H, d, J=15.48 Hz), 7.91 (1H, d, J=6.68 Hz), 8.00 (1H, s), 8.17 (1H, s)

Preparation 76

(2E)-3-(5-{[(3R)-1-(2-cyclohexylethyl)-3-pyrrolidinyl]amino}-2-pyrazinyl)acrylic acid ESI-MS; 383 (M+K)+, 367 (M+Na)+, 345 (M+H)+

¹H-NMR (DMSO-d₆, δ): 6.46 (1H, d, J=15.50 Hz), 7.47 (1H, d, J=15.50 Hz), 7.97 (1H, d, J=6.32 Hz), 8.02 (1H, s), 8.18 (1H, s)

Preparation 77

(2E)-3-(5-{[(3R)-1-(2-cyclopentylethyl)-3-piperidinyl]amino}-2-pyrazinyl)acrylic acid ESI-MS; 383 (M+K)+, 367 (M+Na)+, 345 (M+H)+

¹H-NMR (DMSO-d₆, δ): 6.46 (1H, d, J=15.48 Hz), 7.43 (1H, d, J=15.48 Hz), 7.63 (1H, d, J=7.60 Hz), 8.03 (1H, s), 8.16 (1H, s)

Preparation 78

(2E)-3-(5-{[(3R)-1-(2-cyclohexylethyl)-3-piperidinyl]amino}-2-pyrazinyl)acrylic acid ESI-MS; 397 (M+K)+, 381M+Na)+, 359 (M+H)+

¹H-NMR (DMSO-d₆, δ): 6.45 (1H, d, J=115.50 Hz), 7.43 (1H, d, J=15.50 Hz), 7.56 (1H, d, J=7.72 Hz), 8.01 (1H, s), 8.16 (1H, s)

Preparation 79

(2E)-3-(5-{[(3R)-1-(2-methyl-2-phenylpropyl)-3-pyrrolidinyl]amino}-2-pyrazinyl)acrylic acid ESI-MS; 399 (M+Na)+, 367 (M+H)+

¹H-NMR (DMSO-d₆, δ): 1.29 (6H, s), 6.45 (1H, d, J=15.46 Hz), 7.47 (1H, d, J=15.46 Hz), 7.99 (1H, s), 8.14 (1H, s)

Preparation 80

(2E)-3-[5-({(3R)-1-[2-(2-chlorophenyl)ethyl]-3-piperidinyl}amino)-2-pyrazinyl]acrylic acid ESI-MS; 411 and 409 (M+Na)+, 389 and 387 (M+H)+

¹H-NMR (DMSO-d₆, δ): 6.46 (1H, d, J=15.50 Hz), 7.16-7.41 (4H, m), 7.45 (1H, d, J=15.50 Hz), 7.64 (1H, d, J=7.72 Hz), 8.03 (1H, s), 8.18 (1H, s)

Preparation 81

(2E)-3-[5-({(3R)-1-[2-(4-chlorophenyl)ethyl]-3-piperidinyl}amino)-2-pyrazinyl]acrylic acid ESI-MS; 411 and 409 (M+Na)+, 389 and 387 (M+H)+

¹H-NMR (DMSO-d₆, δ): 6.45 (1H, d, J=15.50 Hz), 7.23-7.33 (4H, m), 7.48 (1H, d, J=15.50 Hz), 7.63 (1H, d, J=7.58 Hz), 8.01 (1H, s), 8.18 (1H, s)

Preparation 82

(2E)-3-(5-{[(3R)-1-(3-cyclohexylpropyl)-3-pyrrolidinyl]amino}-2-pyrazinyl)acrylic acid ESI-MS; 381 (M+Na)+, 359 (M+H)+

¹H-NMR (DMSO-d₆, δ): 6.46 (1H, d, J=15.50 Hz), 7.47 (1H, d, J=15.50 Hz), 7.97 (1H, d, J=6.56 Hz), 8.02 (1H, s), 8.18 (1H, s)

Preparation 83

To a mixture of crude (2E)-3-[5-({(3R)-1-[3-phenylpropyl]- 3-piperidinyl}amino)-2-pyrazinyl] acrylic acid (345 mg), O-(tetrahydro-2H-pyran-2-yl)hydroxylamine (166 mg), and HOBT in dichloromethane (8.6 mL) was added WSCD (271 mg), which was stirred at room temperature for 17 hours. Water was added to the resultant. The organic layer was extracted and dried over $Na_2SO_4$, filtered, and evaporated in vacuo. The residue was purified by column chromatography on silica gel [chromatorexNH, 5 g, hexane:AcOEt=25:75) to give (2E)-3-[5-({(3R)-1-[3-phenylpropyl]-3-piperidinyl}amino)-2-pyrazinyl]-N-(tetrahydro-2H-pyran-2-yloxy)acrylamide (277 mg) as a pale yellow solid.

ESI-MS; 953 (2M+Na)+, 488 (M+Na)+, 466 (M+H)+
$^1$H-NMR (CDCl$_3$, δ): 0.81-0.88 (2H, m), 1.23-1.35 (2H, m), 1.50-2.10 (11H, m), 2.28 (2H, t, J=7.24 Hz), 2.55-2.60 (3H, m), 2.80-2.85 (1H, m), 3.87-4.00 (2H, m), 4.90 (1H, s), 6.60 (1H, d, J=15.20 Hz), 7.13-7.19 (3H, m), 7.23-7.28 (2H, m), 7.39 (1H, d, J=15.20 Hz), 7.46 (1H, d, J=7.44 Hz), 7.99 (1H, s), 8.11 (1H, s)

The following compounds were obtained in a similar manner to that of Preparation 83.

Preparation 84

(2E)-3-[5-({(3R)-1-[2-(2-chlorophenyl)ethyl]-3-pyrrolidinyl}amino)-2-pyrazinyl]-N-(tetrahydro-2H-pyran-2-yloxy)acrylamide m.p.: 146-148° C.
ESI-MS; 967 and 965 (2M+Na)+; 496 and 494 (M+Na)+, 474 and 472 (M+H)+
$^1$H-NMR (DMSO-d$_6$, δ): 1.48-1.72 (7H, m), 2.18-2.29 (1H, m), 2.42-2.92 (8H, m), 3.50-3.58 (1H, m), 3.92-4.00 (1H, m), 4.28-4.36 (1H, m), 4.90 (1H, s), 6.60 (1H, d, J=15.20 Hz), 7.21-7.29 (2H, m), 7.36-7.42 (3H, m), 7.78 (1H, d, J=6.56 Hz), 7.98 (1H, s), 8.12 (1H, s), 11.18 (1H, s))

Preparation 85

(2E)-3-[5-({(3R)-1-[2-(4-chlorophenyl)ethyl]-3-pyrrolidinyl}amino)-2-pyrazinyl]-N-(tetrahydro-2H-pyran-2-yloxy)acrylamide m.p.: 178-180° C.
ESI-MS; 967 and 965 (2M+Na)+, 496 and 494 (M+Na)+, 474 and 472 (M+H)+
$^1$H-NMR (DMSO-d$_6$, δ): 2.48-2.77 (7H, m), 2.14-2.25 (1H, m), 2.42-2.82 (8H, m), 3.50-3.57 (1H, m), 3.90-4.00 (1H, m), 4.25-4.35 (1H, m), 4.90 (1H, s), 6.60 (1H, d, J=15.22 Hz), 7.24-7.34 (4H,), 7.39 (1H, d, J=15.22 Hz), 7.75 (1H, d, J=6.60 Hz), 7.97 (1H, s), 8.11 (1H, s), 11.18 (1H, s)

Preparation 86

(2E)-3-[5-({(3R)-1-[2-(4-methoxyphenyl)ethyl]-3-pyrrolidinyl}amino)-2-pyrazinyl]-N-(tetrahydro-2H-pyran-2-yloxy)acrylamide m.p.: 167-169° C.
ESI-MS; 490 (M+Na)+, 468 (M+H)+
$^1$H-NMR (DMSO-d$_6$, δ): 2.48-2.77 (7H, m), 2.17-2.28 (1H, m), 2.42-2.84 (8H, m), 3.48-3.60 (1H, m), 3.71 (3H, s), 3.90-4.00 (1H, m), 4.25-4.36 (1H, m), 4.90 (1H, s), 6.60 (1H, d, J=15.20 Hz), 6.80-6.85 (2H, m), 7.11-7.15 (2H, m), 7.39 (1H, d, J=15.20 Hz), 7.76 (1H, d, J=6.52 Hz), 7.98 (1H, s), 8.11 (1H, s), 11.18 (1H, s)

Preparation 87

(2E)-3-[5-({(3R)-1-[2-(4-bromophenyl)ethyl]-3-pyrrolidinyl}amino)-2-pyrazinyl]-N-(tetrahydro-2H-pyran-2-yloxy)acrylamide m.p.: 183-185° C.
ESI-MS; 540 and 538 (M+Na)+, 518 and 516 (M+H)+
$^1$H-NMR (DMSO-d$_6$, δ): 2.48-2.77 (7H, m), 2.11-2.25 (1H, m), 2.40-2.85 (8H, m), 2.47-2.55 (1H, m), 2.88-4.00 (1H, m), 4.25-4.34 (1H, m), 4.90 (1H, s), 6.60 (1H, d, J=15.22 Hz), 7.20 (2H, d, J=8.26 Hz), 7.39 (1H, d, J=15.22 Hz), 7.45 (2H, d, J=8.26 Hz), 7.75 (1H, d, J=6.28 Hz), 7.97 (1H, s), 8.11 (1H, s), 11.18 (1H, s)

Preparation 88

(2E)-3-(5-{[(3R)-1-(2-cyclopentylethyl)-3-pyrrolidinyl]amino}-2-pyrazinyl)-N-(tetrahydro-2H-pyran-2-yloxy)acrylamide ESI-MS; 468 (M+K)+, 452 (M+Na)+, 430 (M+H)+
$^1$H-NMR (DMSO-d$_6$, δ): 0.98-1.1.12 (2H, m), 1.38-1.82 (16H, m), 2.10-2.22 (1H, m), 2.28-2.45 (4H, m), 2.60-2.74 (2H, m), 3.50-3.54 (1H, m), 3.91-4.03 (1H, m), 4.23-4.32 (1H, m), 4.90 (1H, s), 6.60 (1H, d, J=15.20 Hz), 7.38 (1H, d, J=15.20 Hz), 7.75 (1H, d, J=6.42 Hz), 7.97 (1H, s), 8.11 (1H, s), 11.18 (1H, s)

Preparation 89

(2E)-3-(5-{[(3R)-1-(2-cyclohexylethyl)-3-pyrrolidinyl]amino}-2-pyrazinyl)-N-(tetrahydro-2H-pyran-2-yloxy)acrylamide ESI-MS; 482 (M+K)+, 466 (M+Na)+, 444 (M+H)+
$^1$H-NMR (DMSO-d$_6$, δ): 0.80-1.95 (2H, m), 1.05-1.38 (6H, m), 1.50-1.80 (12H, m), 2.10-2.24 (1H, m), 2.30-2.45 (4H, m), 2.50-2.75 (2H, m), 3.50-3.54 (1H, m), 3.98-4.00 (1H, m), 4.22-4.34 (1H, m), 4.89 (1H, s), 6.58 (1H, d, J=15.26 Hz), 7.38 (1H, d, J=15.28 Hz), 7.75 (1H, d, J=6.36 Hz), 7.97 (1H, s), 8.11 (1H, s), 11.81 (1H, s)

Preparation 90

(2E)-3-(5-{[(3R)-1-(2-cyclopentylethyl)-3-piperidinyl]amino}-2-pyrazinyl)-N-(tetrahydro-2H-pyran-2-yloxy)acrylamide ESI-MS; 482 (M+K)+, 446 (M+Na)+, 444 (M+H)+
$^1$H-NMR (DMSO-d$_6$, δ): 0.95-2.30 (25H, m), 2.60-2.68 (1H, m), 2.80-2.90 (1H, m), 3.50-3.58 (1H, m), 3.85-4.00 (2H, m), 4.90 (1H, s), 6.59 (1H, d, J=15.28 Hz), 7.38 (1H, d, J=15.28 Hz), 7.44 (1H, d, J=7.60 Hz), 7.98 (1H, s), 8.10 (1H, s), 11.18 (1H, s)

Preparation 91

(2E)-3-(5-{[(3R)-1-(2-cyclohexylethyl)-3-piperidinyl]amino}-2-pyrazinyl)-N-(tetrahydro-2H-pyran-2-yloxy)acrylamide ESI-MS; 480 (M+Na)+, 458 (M+H)+
$^1$H-NMR (DMSO-d$_6$, δ): 0.80-0.90 (2H, m), 1.08-2.00 (23H, m), 2.25-2.30 (2H, m), 2.58-2.67 (1H, m), 2.84-2.89

(1H, m), 3.48-3.58 (1H, m), 3.85-4.00 (2H, m), 4.90 (1H, s), 6.59 (1H, d, J=15.32 Hz), 7.38 (1H, d, J=15.32 Hz), 7.44 (1H, d, J=7.58 Hz), 7.98 (1H, s), 8.10 (1H, s), 11.17 (1H, s)

Preparation 92

(2E)-3-(5-{[(3R)-1-(2-methyl-2-phenylpropyl)-3-pyrrolidinyl]amino}-2-pyrazinyl)-N-(tetrahydro-2H-pyran-2-yloxy)acrylamide ESI-MS; 466 (M+H)+
$^1$H-NMR (DMSO-d$_6$, δ) 1.5-2.7 (14H, m), 3.5-4.9 (4H, m), 6.59 (1H, d, J=15.44 Hz), 7.1-7.4 (6H, m), 7.59 (1H, d, J=6.60 Hz), 7.94 (1H, s), 8.06 (1H, s), 11.17 (1H, br.s)

Preparation 93

(2E)-3-[5-({(3R)-1-[2-(2-chlorophenyl)ethyl]-3-piperidinyl}amino)-2-pyrazinyl]-N-(tetrahydro-2H-pyran-2-yloxy)acrylamide ESI-MS; 510 and 508 (M+Na)+, 488 and 486 (M+H)+
$^1$H-NMR (DMSO-d$_6$, δ): 4.90 (1H, s), 6.60 (1H, d, J=15.28 Hz), 7.22-7.41 (5H, m), 7.47 (1H, d, J=7.56 Hz), 8.00 (1H, s), 8.12 (1H, s), 11.18 (1H, br.s)

Preparation 94

(2E)-3-[5-({(3R)-1-[2-(4-chlorophenyl)ethyl]-3-piperidinyl}amino)-2-pyrazinyl]-N-(tetrahydro-2H-pyran-2-yloxy)acrylamide ESI-MS; 510 and 508 (M+Na)+, 488 and 486 (M+H)+
$^1$H-NMR (DMSO-d$_6$, δ): 4.90 (1H, s), 6.60 (1H, d, J=15.26 Hz), 7.23-7.33 (4H, m), 7.39 (1H, d, J=15.26 Hz), 7.45 (1H, d, J=7.52 Hz), 7.98 (1H, s), 8.12 (1H, s), 11.17 (1H, br.s)

Preparation 95

(2E)-3-(5-{[(3R)-1-(3-cyclohexylpropyl)-3-pyrrolidinyl]amino}-2-pyrazinyl)-N-(tetrahydro-2H-pyran-2-yloxy)acrylamide ESI-MS; 480 (M+Na)+, 458 (M+H)+
$^1$H-NMR (DMSO-d$_6$, δ): 0.81-0.85 (2H, m), 1.04-2.09 (20H, m), 2.12-2.72 (7H, m), 3.50-3.54 (1H, m), 3.94-3.97 (1H, m), 4.27-4.30 (1H, m), 4.90 (1H, s), 6.60 (1H, d, J=15.20 Hz), 7.38 (1H, d, J=15.20 Hz), 7.74 (1H, d, J=6.48 Hz), 7.97 (1H, s), 8.11 (1H, s), 11.17 (1H, br.s)

Preparation 96

A solution of 1M DIBAL solution of toluene (1.65 mL) was added dropwise to a solution of 2-(2-chlorophenyl)-N-methoxy-N-methylacetamide (320 mg) in THF (6 mL) under −40° C. and stirred at the same temperature for 30 minutes. After addition of 1N—HCl aq. (10 mL), the mixture was stirred at 20-25° C. for 30 minutes, extracted with IPE, dried over magnesium sulfate and concentrated reduced pressure to give a residue. To a solution of the residue in dichloromethane (6 mL), methyl (2E)-3-{5-[(3R)-3-pyrrolidinylamino]-2-pyrazinyl}acrylate dihydrochloride (322 mg), DIEA (0.35 mL) and sodium triacetoxyborohydride (424 mg) was added and the mixture was stirred at 20-25° C. for 3 hours. After addition of saturated aqueous sodium hydrogen carbonate, the mixture was stirred at the same temperature for 30 minutes. An organic layer was washed with water, dried over magnesium sulfate and concentrated under reduced pressure to give methyl (2E)-3-[5-({(3R)-1-[2-(2-chlorophenyl)ethyl]-3-pyrrolidinyl}amino)-2-pyrazinyl] acrylate.

m.p.: 113-114.5° C.
ESI-MS; 411 and 409 (M+Na)+, 389 and 387 (M+H)+
$^1$H-NMR (DMSO-d$_6$, δ): 1.60-1.70 (1H, m), 2.18-2.28 (1H, m), 2.45-2.92 (8H, m), 3.70 (3H, s), 4.31-4.35 (1H, m), 6.52 (1H, d, J=15.52 Hz), 7.20-7.30 (2H, m), 7.36-7.42 (2H, m), 7.57 (1H, d, J=15.52 Hz), 7.95 (1H, d, J=6.64 Hz), 8.01 (1H, s), 8.23 (1H, s)

The following compounds were obtained in a similar manner to that of Preparation 96.

Preparation 97

Methyl (2E)-3-[5-({(3R)-1-[2-(4-chlorophenyl)ethyl]-3-pyrrolidinyl}amino)-2-pyrazinyl]acrylate m.p.: 123-124.5° C.
ESI-MS; 411 and 409 (M+Na)+, 389 and 387 (M+H)+
$^1$H-NMR (DMSO-d$_6$, δ): 1.58-2.69 (1H, m), 2.15-2.25 (1H, m), 2.40-2.85 (8H, m), 3.70 (3H, s), 4.28-4.35 (1H, m), 6.52 (1H, d, J=15.52 Hz), 7.24-7.27 (2H, m), 7.30-7.34 (2H; m), 7.57 (1H, d), 7.93 (1H, d, J=6.68 Hz), 8.00 (1H, s), 8.22 (1H, s))

Preparation 98

Methyl (2E)-3-[5-({(3R)-1-[2-(4-methoxyphenyl)ethyl]-3-pyrrolidinyl}amino)-2-pyrazinyl]acrylate m.p.: 138.5-140.5° C.
ESI-MS; 405 (M+Na)+, 383 (M+H)+
$^1$H-NMR (DMSO-d$_6$, δ): 1.60-1.70 (1H, m), 2.15-2.25 (1H, m), 2.40-2.80 (8H, m), 3.70 (3H, s), 3.71 (3H, s), 4.25-4.35 (1H, m), 6.52 (1H, d, J=15.50 Hz), 6.81-6.84 (2H, m), 7.10-7.14 (2H, m), 7.57 (1H, d, J=15.50 Hz), 7.93 (1H, d, J=6.66 Hz), 8.00 (1H, s), 8.22 (1H, s)

Preparation 99

Methyl (2E)-3-[5-({(3R)-1-[2-(4-bromophenyl)ethyl]-3-pyrrolidinyl}amino)-2-pyrazinyl]acrylate m.p.: 129-130.5° C.
ESI-MS; 433 and 431 (M+H)+
$^1$H-NMR (DMSO-d$_6$, δ): 1.60-1.70 (1H, m), 2.15-2.25 (1H, m), 2.42-2.82 (8H, m), 3.70 (3H, s), 4.27-4.38 (1H, m), 6.52 (1H, d, J=15.52 Hz), 7.18-7.22 (2H, m), 7.43-7.47 (2H, m), 7.57 (1H, d, J=15.52 Hz), 7.93 (1H, d, J=6.64 Hz), 8.00 (1H, s), 8.22 (1H, s)

Preparation 100

A solution of 1M DIBAL solution of toluene (2.31 mL) was added dropwise to absolution of methyl cyclopentylacetate (299 mg) in diethyl ether (8.4 mL) under −30° C. and stirred at the same temperature for 1 hour. After addition of 1N—HCl aq. (15 mL), the mixture was stirred at 20-25° C. for 30 minutes, extracted with diethyl ether, dried over magnesium sulfate and concentrated under reduced pressure to give a residue. To a solution of the residue in dichloromethane (5.6 mL), methyl (2E)-3-{5-[(3R)-3-pyrrolidinylamino]-2-pyrazinyl}acrylate dihydrochloride (450 mg), DIEA (0.49 mL) and sodium triacetoxyborohydride (594 mg) was added and the mixture was stirred at 20-25° C. for 3 hours. After addition of saturated aqueous sodium hydrogen carbonate, the mixture was stirred at the same temperature for 30 minutes. An organic layer was washed with water, dried over magnesium sulfate and concentrated under reduced pressure to give a solid. The solid was purified by silica gel (chromatorex NH) (hexane-AcOEt 70:30 v/v) to give a solid (429 mg). The solid was triturated with acetone —IPE and collected by filtration to give methyl (2E)-3-(5-{[(3R)-1-(2-cyclopentylethyl)-3-pyrrolidinyl]amino}-2-pyrazinyl)acrylate (365 mg).

ESI-MS; 345 (M+H)+

$^1$H-NMR (DMSO-$d_6$, δ): 0.97-1.14 (2H, m), 1.40-1.80 (10H, m), 2.15-2.25 (1H, m), 2.29-2.45 (4H, m), 2.60-2.72 (2H, m), 3.70 (3H, s), 4.23-4.32 (1H, m), 6.51 (1H, d, J=15.50 Hz), 7.56 (1H, d, J=15.50 Hz), 7.91 (1H, d, J=6.68 Hz), 8.00 (1H, s), 8.21 (1H, s)

The following compounds were obtained in a similar manner to that of Preparation 100.

Preparation 101

Methyl (2E)-3-(5-{[(3R)-1-(2-cyclohexylethyl)-3-pyrrolidinyl]amino}-2-pyrazinyl)acrylate ESI-MS; 381 (M+Na)+, 359 (M+H)+

$^1$H-NMR (DMSO-$d_6$, δ): 1.31-1.42 (1H, m), 1.01-1.35 (6H, m), 1.57-1.73 (6H, m), 2.14-2.24 (1H, m), 2.30-2.45 (4H, m), 2.60-2.74 (2H, m), 3.70 (3H, s), 4.25-4.34 (1H, m), 6.51 (1H, d, J=15.50 Hz), 7.56 (1H, d, J=15.50 Hz), 7.92 (1H, d, J=6.64 Hz), 7.99 (1H, s), 8.22 (1H, s)

Preparation 102

Methyl (2E)-3-(5-{[(3R)-1-(2-cyclopentylethyl)-3-piperidinyl]amino}-2-pyrazinyl)acrylate

ESI-MS; 359 (M+H)+

$^1$H-NMR (DMSO-$d_6$, δ): 0.99-1.11 (2H, m), 1.22-1.32 (1H, m), 1.40-1.51 (7H, m), 1.62-2.10 (7H, m), 2.25-2.29 (2H, m), 2.58-2.67 (1H, m), 2.81-2.86 (1H, m), 3.70 (3H, s), 3.88-3.97 (1H, m), 6.50 (1H, d, J=15.50 Hz), 7.56 (1H, d, J=15.50 Hz), 7.61 (1H, d, J=7.72 Hz), 8.01 (1H, s), 8.21 (1H, s)

Preparation 103

Methyl (2E)-3-(5-{[(3R)-1-(2-cyclohexylethyl)-3-piperidinyl]amino}-2-pyrazinyl)acrylate ESI-MS; 395 (M+Na)+, 373 (M+H)+

$^1$H-NMR (DMSO-$d_6$, δ): 0.80-1.95 (2H, m), 1.02-2.08 (17H, m), 2.25-2.30 (2H, m), 2.55-2.65 (1H, m), 2.76-2.85 (1H, m), 3.70 (3H, s), 3.85-3.98 (1H, m), 6.51 (1H, d, J=15.48 Hz), 7.56 (1H, d, J=15.48 Hz), 7.61 (1H, d, J=7.64 Hz), 8.01 (1H, s), 8.21 (1H, s)

Preparation 104

Methyl (2E)-3-(5-{[(3R)-1-(2-methyl-2-phenylpropyl)-3-pyrrolidinyl]amino}-2-pyrazinyl)acrylate

ESI-MS; 381 (M+H)+

$^1$H-NMR (DMSO-$d_6$, δ): 1.28 (6H, s), 1.43-1.58 (1H, m), 1.98-2.10 (1H, m), 2.20-2.32 (2H, m), 2.42-2.53 (1H, m), 2.58-2.70 (3H, m), 3.69 (3H, s), 4.12-4.22 (1H, m), 6.50 (1H, d, J=15.56 Hz), 7.10-7.15 (1H, m), 7.22-7.27 (2H, m), 7.35-7.39 (2H, m), 7.55 (1H, d, J=15.56 Hz), 7.78 (1H, d, J=6.72 Hz), 7.96 (1H, s), 8.17 (1H, s)

Preparation 105

Methyl (2E)-3-(5-{[(3R)-1-(3-cyclohexylpropyl)-3-pyrrolidinyl]amino}-2-pyrazinyl)acrylate

ESI-MS; 373 (M+H)+

$^1$H-NMR (DMSO-$d_6$, δ): 0.78-0.88 (2H, m), 1.50-2.22 (6H, m), 1.37-1.46 (2H, m), 1.56-1.70 (6H, m), 2.15-2.23 (1H, m), 2.30-2.44 (4H, m), 2.61-2.71 (2H, m), 3.70 (3H, s), 4.26-4.33 (1H, m), 6.51 (1H, d, J=15.50 Hz), 7.56 (1H, d, J=15.50 Hz), 7.91 (1H, d, J=6.68 Hz), 8.00 (1H, s), 8.21 (1H, s)

Preparation 106

To a cooled solution of methyl 2-chlorophenylacetate (388 mg) in THF (8.4 mL) at −40° C. was added dropwise a solution of 1.0M DIBAL in hexane (2.34 mL) below −30° C. under nitrogen atmosphere. After stirring for 3 hours under −30° C., 1N—HCl aq. (15 mL) was added to the reaction mixture. After stirring for 30 minutes at ambient temperature, IPE (15 ml) was added. The organic layer was separated, washed with water (15 ml), dried over MgSO$_4$ and evaporated in vacuo. To a solution of the residue and methyl (2E)-3-{5-[(3R)-3-piperidinylamino]-2-pyrazinyl}acrylate dihydrochloride (470 mg) in dichloromethane (5.6 ml) was added NaBH(OAc)$_3$ (594 mg) and DIEA (0.49 ml). The mixture was stirred for 4 hours at ambient temperature and added aqueous NaHCO$_3$ and CH$_2$Cl$_2$. After stirring for 0.5 hours, the organic layer was separated, washed with water, dried over MgSO$_4$, and evaporated in vacuo. The residue was chromatographed on silica gel (hexane:AcOEt=75:25). The desired fractions were collected and evaporated in vacuo. Crystallization from IPE and hexane gave methyl (2E)-3-[5-[{(3R)-1-[2-(2-chlorophenyl)ethyl]-3-piperidinyl}amino]-2-pyrazinyl]acrylate (310 mg) as a pale yellow crystal.

ESI-MS; 403 and 401 (M+H)+

$^1$H-NMR (DMSO-$d_6$, δ): 1.28-1.34 (1H, m), 1.47-1.58 (1H, m), 1.68-1.78 (1H, m), 1.80-1.90 (1H, m), 2.02-2.10 (1H, m), 2.10-2.20 (1H, m), 2.50-2.55 (2H, m), 2.70-2.78 (1H, m), 2.82-2.90 (2H, m), 2.90-3.00 (1H, m), 3.70 (3H, s), 3.90-4.01 (1H, m), 6.51 (1H, d, J=15.54 Hz), 7.20-7.28 (2H, m), 7.35-7.41 (2H, m), 7.578 (1H, d, J=15.54 Hz), 7.64 (1H, d, J=7.74 Hz), 8.02 (1H, s), 8.23 (1H, s)

The following compound was obtained in a similar manner to that of Preparation 106.

Preparation 107

Methyl (2E)-3-[5-({(3R)-1-[2-(4-chlorophenyl)ethyl]-3-piperidinyl}amino)-2-pyrazinyl]acrylate ESI-MS; 403 and 401 (M+H)+

$^1$H-NMR (DMSO-$d_6$, δ): 1.27-1.35 (1H, m), 1.44-1.55 (1H, m), 1.68-1.75 (1H, m), 1.79-1.87 (1H, m), 1.95-2.04 (1H, m), 2.07-2.15 (1H, m), 2.50-2.54 (2H, m), 2.69-2.74 (3H, m), 2.90-2.97 (1H, m), 3.70 (3H, s), 3.90-3.99 (1H, m), 6.51 (1H, d, J=15.44 Hz), 7.23-7.26 (2H, m), 7.29-7.33 (2H, m), 7.57 (1H, d, J=15.44 Hz), 7.62 (1H, d, J=7.72 Hz), 8.01 (1H, s), 8.23 (1H, s)

EXAMPLE 1

A solution of (2E)-3-[5-({(3R)-1-[2-(3-fluorophenyl)ethyl]-3-pyrrolidinyl}amino)-2-pyrazinyl]-N-(tetrahydro- 2H-pyran-2-yloxy)acrylamide (160 mg) in EtOH (1.6 mL) was added 2N—HCl solution in EtOH (0.9 mL) and stirred for 3 hours at ambient temperature. The solvent was evaporated in vacuo. To the residue was added IPE. The resulting solid was collected by the filtration to give (2E)-3-[5-({(3R)-1-[2-(3-fluorophenyl)ethyl]-3-pyrrolidinyl}amino)-2-pyrazinyl]-N-hydroxyacrylamide dihydrochloride (116 mg).

ESI-MS; 372 (M+H)+
$^1$H-NMR (DMSO-$d_6$, δ); 2.01-3.93 (11H, m), 6.64 (1H, d, J=15 Hz), 7.09-7.42 (6H, m), 8.05-8.16 (3H, m), 11.08-11.16 (1H, m)

The following compounds were obtained in a similar manner to that of Example 1.

EXAMPLE 2

(2E)-3-[5-({(3R)-1-[2-(2,4-difluorophenyl)ethyl]-3-pyrrolidinyl}amino)-2-pyrazinyl]-N-hydroxyacrylamide dihydrochloride ESI-MS; 390 (M+H)+
$^1$H-NMR (DMSO-$d_6$, δ); 1.9-4.18 (11H, m), 6.61-8.26 (8H, m), 11.22-11.34 (1H, m)

EXAMPLE 3

(2E)-3-[5-({(3R)-1-[2-(2,6-difluorophenyl)ethyl]-3-pyrrolidinyl}amino)-2-pyrazinyl]-N-hydroxyacrylamide dihydrochloride ESI-MS; 390 (M+H)+
$^1$H-NMR (DMSO-$d_6$, δ); 2.0-4.58 (11H, m), 6.62-6.66 (1H, m), 7.11-7.15 (2H, m), 7.36-7.44 (2H, m), 8.06 (1H, s), 8.16 (1H, s), 11.24-11.39 (1H, m)

EXAMPLE 4

(2E)-N-hydroxy-3-[5-({(3R)-1-[2-(2-thienyl)ethyl]-3-pyrrolidinyl}amino)-2-pyrazinyl]acrylamide dihydrochloride ESI-MS; 360 (M+H)+
$^1$H-NMR (DMSO-$d_6$, δ); 2.0-4.57 (11H, m), 6.61-8.23 (9H, m), 11.15-11.26 (1H, m)

EXAMPLE 5

(2E)-3-[5-({(3R)-1-[2-(3,4-difluorophenyl)ethyl]-3-pyrrolidinyl}amino)-2-pyrazinyl]-N-hydroxyacrylamide dihydrochloride ESI-MS; 390 (M+H)+
$^1$H-NMR (DMSO-$d_6$, δ); 1.9-4.18 (11H, m), 6.63 (1H, d, J=15 Hz), 7.14-7.43 (4H, m), 8.05-8.28 (3H, m), 11.16-11.24 (1H, m)

EXAMPLE 6

(2E)-3-[5-({(3R)-1-[2-(3-fluorophenyl)ethyl]-3-piperidinyl}amino)-2-pyrazinyl]-N-hydroxyacrylamide dihydrochloride ESI-MS; 386 (M+H)+
$^1$H-NMR (DMSO-$d_6$, δ); 1.9-4.18 (13H, m), 6.64 (1H, d, J=15.3 Hz), 7.06-7.18 (5H, m), 7.4 (1H, d, J=15.3 Hz), 8.05 (1H, s), 8.17 (1H, s), 10.92 (1H, br.s)

EXAMPLE 7

(2E)-3-[5-({(3R)-1-[2-(2-fluorophenyl)ethyl]-3-piperidinyl}amino)-2-pyrazinyl]-N-hydroxyacrylamide dihydrochloride ESI-MS; 386 (M+H)+
$^1$H-NMR (DMSO-$d_6$, δ); 1.98-4.18 (13H), 6.63 (1H, d, J=15 Hz), 7.17-8.16 (9H, m)

EXAMPLE 8

(2E)-3-[5-({(3R)-1-[2-(2,4-difluorophenyl)ethyl]-3-piperidinyl}amino)-2-pyrazinyl]-N-hydroxyacrylamide dihydrochloride ESI-MS; 404 (M+H)+
$^1$H-NMR (DMSO-$d_6$, δ); 1.98-4.18 (13H, m), 6.5-11 (8H, m)

EXAMPLE 9

(2E)-3-[5-({(3R)-1-[2-(3,4-difluorophenyl)ethyl]-3-piperidinyl}amino)-2-pyrazinyl]-N-hydroxyacrylamide dihydrochloride ESI-MS; 404 (M+H)+
$^1$H-NMR (DMSO-$d_6$, δ); 1.9-4.18 (13H, m), 6.6-6.67 (1H, m), 7.1-7.2 (1H, m), 7.3-7.4 (3H, m), 8.0-8.1 (2H, m), 10.5-10.9 (1H, m)

EXAMPLE 10

To a solution of (2E)-3-[5-({(3R)-1-[2-(dimethylamino)benzyl]-3-pyrrolidinyl}amino)-2-pyrazinyl]-N-(tetrahydro-2H-pyran-2-yloxy)acrylamide (236 mg) in MeOH (3.5 mL) was added 2N—HCl solution in EtOH (1.27 mL), which was stirred at room temperature for 1 hour. To the reaction mixture was dropwised IPE (9.4 mL), which was stirred further more 1 hour. The prepicitate was filtered to give (2E)-3-[5-({(3R)-1-[2-(dimethylamino) benzyl]-3-pyrrolidinyl}amino)-2-pyrazinyl]-N-hydroxyacrylamide trihydrochloride as a yellow powder (241 mg).

$^1$H-NMR (DMSO-$d_6$, δ): 2.01-2.14 (1H, m), 2.36-2.52 (1H, m), 2.93 (6H, br), 3.28 (1H, br), 3.47 (1H, br), 3.57 (1H, br), 3.66-4.92 (4H, m), 6.63 (1H, d, J=15.1 Hz), 7.39 (1H, d, J=15.1 Hz), 7.35-7.45 (1H, b), 7.51-7.73 (2H, m), 7.80-7.90 (1H, br, m), 8.01-8.34 (3H, m), 11.16 (1H, br).

ESI-MS; 383 (M+H)+.

The following compounds were obtained in a similar manner to that of Example 10.

EXAMPLE 11

(2E)-3-(5-{[(3R)-1-(4-fluoro-3-methoxybenzyl)-3-pyrrolidinyl]amino}-2-pyrazinyl)-N-hydroxyacrylamide dihydrochloride $^1$H-NMR (DMSO-$d_6$, δ): 1.94-2.14 (1H, m), 2.24-2.57 (1H, m), 2.98-4.80 (10H, m), 6.62 (1H, dd, J=2.0, 15.1 Hz), 7.11-7.18 (1H, m), 7.23-7.31 (1H, m), 7.39 (1H, d, J=15.1 Hz), 7.61 (1H, d, J=8.4 Hz), 7.99-8.39 (3H, m), 11.45 (1H, br).

ESI-MS; 388 (M+H)+.

EXAMPLE 12

(2E)-3-(5-{[(3R)-1-(cyclopentylmethyl)-3-pyrrolidinyl]amino}-2-pyrazinyl)-N-hydroxyacrylamide dihydrochloride $^1$H-NMR (DMSO-d$_6$, δ): 1.18-1.32 (2H, m), 1.42-1.66 (4H, m), 1.75-1.88 (2H, m), 1.96-2.09 (1H, m), 2.12-2.57 (2H, m), 2.94-5.13 (7H, m), 6.63 (1H, d, J=15.6 Hz), 7.39 (1H, d, J=15.6 Hz), 8.01-8.56 (3H, m), 10.65 (1H, br).

ESI-MS; 332 (M+H)+.

EXAMPLE 13

(2E)-N-hydroxy-3-(5-{[(3R)-1-{[1-(hydroxymethyl)cyclohexyl]methyl}-3-pyrrolidinyl]amino}-2-pyrazinyl)acrylamide dihydrochloride $^1$H-NMR (DMSO-d$_6$, δ): 1.27-1.52 (10H, m), 1.98-2.10 (1H, m), 2.30-2.52 (1H, m), 3.10-4.11 (9H, m), 4.47-4.64 (1H, m), 6.64 (1H, d, J=15.3 Hz), 7.39 (1H, dd, J=2.0, 15.3 Hz), 8.02-8.46 (3H, m), 9.81 (1H, br).

ESI-MS; 376 (M+H)+.

EXAMPLE 14

(2E)-N-hydroxy-3-(5-{[(3R)-1-(7-oxabicyclo[2.2.1]hept-1-ylmethyl)-3-pyrrolidinyl]amino}-2-pyrazinyl)acrylamide dihydrochloride $^1$H-NMR (DMSO-d$_6$, δ): 1.48-1.83 (8H, m), 1.99-2.11 (1H, m), 2.30-2.57 (1H, m), 3.09-4.06 (7H, m), 4.48-4.66 (2H, m), 6.65 (1H, d, J=15.3 Hz), 7.40 (1H, d, J=15.3 Hz), 8.02-8.52 (3H, m), 10.68-10.91 (1H, m).

ESI-MS; 360 (M+H)+.

EXAMPLE 15

(2E)-3-(5-{[(3R)-1-(5-fluoro-2-methoxybenzyl)-3-pyrrolidinyl]amino}-2-pyrazinyl)-N-hydroxyacrylamide dihydrochloride $^1$H-NMR (DMSO-d$_6$, δ): 1.96-2.15 (1H, m), 2.26-2.55 (1H, m), 3.07-3.81 (4H, m), 3.78-3.85 (3H, m), 4.33-4.66 (3H, m), 6.64 (1H, dd, J=3.1, 15.3 Hz), 7.07-7.17 (1H, m), 7.23-7.33 (1H, m), 7.39 (1H, d, J=15.3 Hz), 7.55 (1H, dd, J=3.1, 9.2 Hz), 8.00-8.43 (3H, m), 11.02 (1H, br).

ESI-MS; 388 (M+H)+.

EXAMPLE 16

A solution of (2E)-3-[5-[{(3R)-1-(1-naphthylmethyl)-3-pyrrolidinyl}amino]-2-pyrazinyl]-N-(tetrahydro-2H-pyran-2-yloxy)acrylamide (350 mg) and 2N—HCl solution in EtOH (10 mL) was stirred for 2 hours at ambient temperature. AcOEt (10 ml) and IPE (50 ml) was added to the reaction mixture. The resulting solid was collected by filtration to give (2E)-N-hydroxy-3-[5-[{(3R)-1-(1-naphthylmethyl)-3-pyrrolidinyl}amino]-2-pyrazinyl]acrylamide dihydrochloride (275 mg).

$^1$H-NMR (DMSO-d$_6$, δ): 1.96-2.17 (2H, m), 2.26-2.62 (2H, m), 3.16-3.41 (2H, m), 4.42-4.67 (1H, m), 4.94 (1H, d, J=2.7 Hz 5 (1H, d, J=2.7 Hz), 6.63 (1H, dd, J=3.6, 7.6 Hz), 7.38 (1H, d, J=7.6 Hz), 7.57-7.7 (3H, m), 7.9 (1H, t, J=3.1 Hz), 8-8.12 (5H, m), 8.38 (1H, t, J=4.1 Hz).

ESI-MS; 390 (M+H)+.

EXAMPLE 17

To a solution of (2E)-3-[5-({(3R)-1-[3-phenylpropyl]-3-piperidinyl}amino)-2-pyrazinyl]-N-(tetrahydro-2H-pyran-2-yloxy)acrylamide (265 mg) in EtOH (1.5 mL) was added 2N—HCl solution in EtOH (1.5 mL). The reaction mixture was stirred for 2 hours at ambient temperature. IPE (1.5 ml) was added to the mixture. The resulting solid was collected by filtration to give (2E)-N-hydroxy-3-[5-[{(3R)-1-(3-phenylpropyl)-3-piperidinyl}amino]-2-pyrazinyl]acrylamide dihydrochloride (148 mg).

$^1$H-NMR (DMSO-d$_6$, δ): 6.62 (1H, d, J=15.24 Hz), 7.39 (1H, d, J=15.24 Hz), 8.03 (1H, s), 8.15 (1H, s)

ESI-MS; 382 (M+H)+

The following compounds were obtained in a similar manner to that of Example 17.

EXAMPLE 18

(2E)-N-hydroxy-3-[5-({(3R)-1-[2-(4-methoxyphenyl)ethyl]-3-pyrrolidinyl}amino)-2-pyrazinyl]acrylamide dihydrochloride $^1$H-NMR (DMSO-d$_6$, δ): 1.94-2.12 (1H, m), 2.21-2.54 (1H, m), 3.73 (3H, s), 2.91-4.3 (8H, m), 4.44-4.61 (1H, m), 6.64 (1H, d, J=15.2 Hz), 6.88-6.92 (2H, m), 7.17-7.23 (2H, m), 7.4 (1H, d, J=15.2 Hz), 8.05-8.25 (3H, m), 10.94-11.13 (1H, m)

ESI-MS; 384 (M+H)+

EXAMPLE 19

(2E)-3-[5-({(3R)-1-[2-(4-bromophenyl)ethyl]-3-pyrrolidinyl}amino)-2-pyrazinyl]-N-hydroxyacrylamide dihydrochloride $^1$H-NMR (DMSO-d$_6$, δ): 6.64 (1H, d, J=15.24 Hz), 7.25-7.29 (2H, m), 6.64 (1H, d, J=15.24 Hz), 7.25-7.55 (2H, m), 8.05-8.25 (3H, m), 11.05-11.25 (1H, br.peak)

ESI-MS; 434 and 432 (M+H)+

EXAMPLE 20

(2E)-3-(5-{[(3R)-1-(2-cyclopentylethyl)-3-pyrrolidinyl]amino}-2-pyrazinyl)-N-hydroxyacrylamide dihydrochloride $^1$H-NMR (DMSO-d$_6$, δ): 6.64 (1H, d, J=15.28 Hz), 7.40 (1H, d, J=15.28 Hz), 8.04 (1H, s), 8.16 (1H, s)

ESI-MS; 346 (M+H)+

EXAMPLE 21

(2E)-3-(5-{[(3R)-1-(2-cyclohexylethyl)-3-pyrrolidinyl]amino}-2-pyrazinyl)-N-hydroxyacrylamide dihydrochloride $^1$H-NMR (DMSO-d$_6$, δ): 6.64 (1H, d, J=15.26 Hz), 7.40 (1H, d, J=15.26 Hz), 8.04 (1H, s), 8.16 (1H,

ESI-MS; 360 (M+H)+

EXAMPLE 22

To a solution of (2E)-3-[5-({(3R)-1-[2-(2-chlorophenyl)ethyl]-3-pyrrolidinyl}amino)-2-pyrazinyl]-N-(tetrahydro-2H-pyran-2-yloxy)acrylamide (95 mg) in EtOH (1 mL) was added a 2N—HCl solution in EtOH (0.5 mL) and the mixture was stirred at 20-25° C. for 2 hours. After removal of EtOH by evaporation, IPE (2 mL) was added to the mixture to give a solid. The solid was collected by filtration and dried under reduced pressure to give (2E)-3-[5-({(3R)-1-[2-(2-chlorophenyl)ethyl]-3-pyrrolidinyl}amino)-2-pyrazinyl]-N-hydroxyacrylamide dihydrochloride (86 mg).

$^1$H-NMR (DMSO-d$_6$, δ): 1.97-2.16 (1H, m), 2.24-2.56 (1H, m), 3.06-4.03 (8H, m), 4.45-4.65 (1H, m), 6.65 (1H, d, J=15.2 Hz 7.29-7.49 (5H, m), 8.06-8.40 (3H, m), 11.30-11.60 (1H, m)

ESI-MS; 390 and 388 (M+H)+

The following compounds were obtained in a similar manner to that of Example 22.

EXAMPLE 23

(2E)-3-[5-({(3R)-1-[2-(4-chlorophenyl)ethyl]-3-pyrrolidinyl}amino)-2-pyrazinyl]-N-hydroxyacrylamide dihydrochloride $^1$H-NMR (DMSO-d$_6$, δ): 1.95-2.15 (1H, m), 2.2-2.56 (1H, m), 3-4 (8H, m), 4.45-4.63 (1H, m), 6.65 (1H, d, J=15.2 Hz), 7.31-7.35 (2H, m), 7.38-7.43 (3H, m), 8.04-8.40 (3H, m), 11.20-11.40 (1H, m)

ESI-MS; 390 and 388 (M+H)+

EXAMPLE 24

(2E)-3-(5-{[(3R)-1-(2-cyclopentylethyl)-3-piperidinyl]amino}-2-pyrazinyl)-N-hydroxyacrylamide dihydrochloride $^1$H-NMR (DMSO-d$_6$, δ): 6.62 (1H, d, J=15.24 Hz), 7.38 (1H, d, J=15.24 Hz), 8.04 (1H, s), 8.14 (1H, s)

ESI-MS; 360 (M+H)+

EXAMPLE 25

(2E)-3-(5-{[(3R)-1-(2-cyclohexylethyl)-3-piperidinyl]amino}-2-pyrazinyl)-N-hydroxyacrylamide dihydrochloride $^1$H-NMR (DMSO-d$_6$, δ): 6.63 (1H, d, J=15.26 Hz), 7.40 (1H, d, J=15.26 Hz), 8.03 (1H, s), 8.15 (1H, s)

ESI-MS; 374 (M+H)+

EXAMPLE 26

(2E)-3-[5-({(3R)-1-[2-(2-chlorophenyl)ethyl]-3-piperidinyl}amino)-2-pyrazinyl]-N-hydroxyacrylamide dihydrochloride $^1$H-NMR (DMSO-d$_6$, δ) 1.45-1.57 (1H, m), 1.78-2.17 (3H, m), 2.66-4.50 (9H, m), 6.63 (1H, d, J=15.4 Hz), 7.30-7.49 (5H, m), 7.86 (1H, b.s), 8.04 (1H, s), 8.17 (1H, s), 10.94 (1H, b.s)

ESI-MS; 404 and 402 (M+H)+

EXAMPLE 27

(2E)-3-[5-({(3R)-1-[2-(4-chlorophenyl)ethyl]-3-piperidinyl}amino)-2-pyrazinyl]-N-hydroxyacrylamide dihydrochloride $^1$H-NMR (DMSO-d$_6$, δ): 1.42-1.57 (1H, m), 1.75-2.18 (3H, m), 2.65-4.46 (9H, m), 6.63 (1H, d, J=15.2 Hz), 7.29-7.34 (2H, m), 7.37-7.43 (2H, m), 7.40 (1H, d, J=15.2 Hz), 7.88 (1H, b.s), 8.05 (1H, s), 8.17 (1H, s), 10.92 (1H, b.s)

ESI-MS; 404 and 402 (M+H)+

EXAMPLE 28

To a solution of (2E)-3-[5-({(3R)-1-[2-methyl-2-phenylpropyl]-3-pyrrolidinyl}amino)-2-pyrazinyl]-N-(tetrahydro-2H-pyran-2-yloxy)acrylamide (130 mg) in EtOH (0.7 mL) was added 2N—HCl solution in EtOH (0.7 mL) and the reaction mixture was stirred for 2 hours at ambient temperature. Acetone was added to the mixture and filtered. The filtrate was evaporated and dried to give (2E)-N-hydroxy-3-[5-[{(3R)-1-(2-methyl-2-phenylpropyl)-3-pyrrolidinyl}amino]-2-pyrazinyl]acrylamide dihydrochloride (108 mg).

$^1$H-NMR (DMSO-d$_6$, δ) 1.47 (3H, s), 1.48 (3H, s), 6.63 (1H, d, J=15.24 Hz)

ESI-MS; 382 (M+H)+

EXAMPLE 29

To a solution of (2E)-3-[5-({(3R)-1-(3-cyclohexylpropyl)-3-pyrrolidinyl}amino)-2-pyrazinyl]-N-(tetrahydro-2H-pyran-2-yloxy)acrylamide (151 mg) in EtOH (0.75 mL) was added 2N—HCl solution in EtOH (0.75 mL) and the reaction mixture was stirred for 2 hours at ambient temperature. The mixture was evaporated and acetone was added. The resulting solid was collected by filtration to give (2E)-3-[5-({(3R)-1-(3-cyclohexylpropyl)-3-pyrrolidinyl}amino)-2-pyrazinyl]-N-hydroxyacrylamide dihydrochloride (117 mg).

$^1$H-NMR (DMSO-d$_6$, δ): 6.64 (1H, d, J=15.3 Hz), 7.40 (1H, d, J=15.3 Hz)

ESI-MS; 374 (M+H)+

The invention claimed is:

1. A compound,
   selected from the group consisting of:
   (2E)-3-(5-{[(3R)-1-(cyclopentylmethyl)-3-pyrrolidinyl]amino}-2-pyrazinyl)-N-hydroxyacrylamide dihydrochloride;
   (2E)-3-[5-({(3R)-1-[2-(dimethylamino)benzyl]-3-pyrrolidinyl}amino)-2-pyrazinyl]-N-hydroxyacrylamide trihydrochloride;
   (2E)-3-(5-{[(3R)-1-(4-fluoro-3-methoxybenzyl)-3-pyrrolidinyl]amino}-2-pyrazinyl)-N-hydroxyacrylamide dihydrochloride;
   (2E)-3-(5-{[(3R)-1-(5-fluoro-2-methoxybenzyl)-3-pyrrolidinyl]amino}-2-pyrazinyl)-N-hydroxyacrylamide dihydrochloride;
   (2E)-3-(5-{[(3R)-1-(2-cyclopentylethyl)-3-pyrrolidinyl]amino}-2-pyrazinyl)-N-hydroxyacrylamide dihydrochloride;
   (2E)-3-(5-{[(3R)-1-(2-cyclopentylethyl)-3-piperidinyl]amino}-2-pyrazinyl)-N-hydroxyacrylamide dihydrochloride;
   (2E)-N-hydroxy-3-(5-{[(3R)-1-{[1-(hydroxymethyl)cyclohexyl]methyl}-3-pyrrolidinyl]amino}-2-pyrazinyl)acrylamide dihydrochloride;

(2E)-3-(5-{[(3R)-1-(2-cyclohexylethyl)-3-pyrrolidinyl]
amino}-2-pyrazinyl)-N-hydroxyacrylamide dihydrochloride;
(2E)-3-(5-{[(3R)-1-(2-cyclohexylethyl)-3-piperidinyl]
amino}-2-pyrazinyl)-N-hydroxyacrylamide dihydrochloride;
(2E)-3-(5-{[(3R)-1-(3-cyclohexylpropyl)-3-pyrrolidinyl]
amino}-2-pyrazinyl)-N-hydroxyacrylamide dihydrochloride;
(2E)-3-[5-({(3R)-1-[2-(3-fluorophenyl)ethyl]-3-pyrrolidinyl}amino)-2-pyrazinyl]-N-hydroxyacrylamide dihydrochloride;
(2E)-3-[5-({(3R)-1-[2-(3-fluorophenyl)ethyl]-3-piperidinyl}amino)-2-pyrazinyl]-N-hydroxyacrylamide dihydrochloride;
(2E)-3-[5-({(3R)-1-[2-(2-fluorophenyl)ethyl]-3-piperidinyl}amino)-2-pyrazinyl]-N-hydroxyacrylamide dihydrochloride;
(2E)-3-[5-({(3R)-1-[2-(2,4-difluorophenyl)ethyl]-3-pyrrolidinyl}amino)-2-pyrazinyl]-N-hydroxyacrylamide dihydrochloride;
(2E)-3-[5-({(3R)-1-[2-(2,6-difluorophenyl)ethyl]-3-pyrrolidinyl}amino)-2-pyrazinyl]-N-hydroxyacrylamide dihydrochloride;
(2E)-3-[5-({(3R)-1-[2-(3,4-difluorophenyl)ethyl]-3-pyrrolidinyl}amino)-2-pyrazinyl]-N-hydroxyacrylamide dihydrochloride;
(2E)-3-[5-({(3R)-1-[2-(2,4-difluorophenyl)ethyl]-3-piperidinyl}amino)-2-pyrazinyl]-N-hydroxyacrylamide dihydrochloride;
(2E)-3-[5-({(3R)-1-[2-(3,4-difluorophenyl)ethyl]-3-piperidinyl}amino)-2-pyrazinyl]-N-hydroxyacrylamide dihydrochloride;
(2E)-3-[5-({(3R)-1-[2-(2-chlorophenyl)ethyl]-3-pyrrolidinyl}amino)-2-pyrazinyl]-N-hydroxyacrylamide dihydrochloride;
(2E)-3-[5-({(3R)-1-[2-(4-chlorophenyl)ethyl]-3-pyrrolidinyl}amino)-2-pyrazinyl]-N-hydroxyacrylamide dihydrochloride;
(2E)-3-[5-({(3R)-1-[2-(2-chlorophenyl)ethyl]-3-piperidinyl}amino)-2-pyrazinyl]-N-hydroxyacrylamide dihydrochloride;
(2E)-3-[5-({(3R)-1-[2-(4-chlorophenyl)ethyl]-3-piperidinyl}amino)-2-pyrazinyl]-N-hydroxyacrylamide dihydrochloride;
(2E)-3-[5-({(3R)-1-[2-(4-bromophenyl)ethyl]-3-pyrrolidinyl}amino)-2-pyrazinyl]-N-hydroxyacrylamide dihydrochloride;
(2E)-N-hydroxy-3-[5-({(3R)-1-[2-(4-methoxyphenyl)ethyl]-3-pyrrolidinyl}amino)-2-pyrazinyl]acrylamide dihydrochloride;
(2E)-N-hydroxy-3-(5-{[(3R)-1-(3-phenylpropyl)-3-piperidinyl]amino}-2-pyrazinyl)acrylamide dihydrochloride;
(2E)-N-hydroxy-3-(5-{[(3R)-1-(2-methyl-2-phenylpropyl)-3-pyrrolidinyl]amino}-2-pyrazinyl)acrylamide dihydrochloride;
(2E)-N-hydroxy-3-(5-{[(3R)-1-(1-naphthylmethyl)-3-pyrrolidinyl]amino}-2-pyrazinyl)acrylamide dihydrochloride;
(2E)-N-hydroxy-3-[5-({(3R)-1-[2-(2-thienyl)ethyl]-3-pyrrolidinyl}amino)-2-pyrazinyl]acrylamide dihydrochloride; and
(2E)-N-hydroxy-3-(5-{[(3R)-1-(7-oxabicyclo[2.2.1]hept-1-ylmethyl)-3-pyrrolidinyl]amino}-2-pyrazinyl)acrylamide dihydrochloride.

2. The compound of claim 1, wherein the compound is (2E)-3-(5-{[(3R)-1-(cyclopentylmethyl)-3-pyrrolidinyl]amino}-2-pyrazinyl)-N-hydroxyacrylamide dihydrochloride.

3. The compound of claim 1, wherein the compound is (2E)-3-[5-({(3R)-1-[2-(dimethylamino)benzyl]-3-pyrrolidinyl}amino)-2-pyrazinyl]-N-hydroxyacrylamide trihydrochloride.

4. The compound of claim 1, wherein the compound is (2E)-3-(5-{[(3R)-1-(4-fluoro-3-methoxybenzyl)-3-pyrrolidinyl]amino}-2-pyrazinyl)-N-hydroxyacrylamide dihydrochloride.

5. The compound of claim 1, wherein the compound is (2E)-3-(5-{[(3R)-1-(5-fluoro-2-methoxybenzyl)-3-pyrrolidinyl]amino}-2-pyrazinyl)-N-hydroxyacrylamide dihydrochloride.

6. The compound of claim 1, wherein the compound is (2E)-3-(5-{[(3R)-1-(2-cyclopentylethyl)-3-pyrrolidinyl]amino}-2-pyrazinyl)-N-hydroxyacrylamide dihydrochloride.

7. The compound of claim 1, wherein the compound is (2E)-3-(5-{[(3R)-1-(2-cyclopentylethyl)-3-piperidinyl]amino}-2-pyrazinyl)-N-hydroxyacrylamide dihydrochloride.

8. The compound of claim 1, wherein the compound is (2E)-N-hydroxy-3-(5-{[(3R)-1-{[1-(hydroxymethyl)cyclohexyl]methyl}-3-pyrrolidinyl]amino}-2-pyrazinyl)acrylamide dihydrochloride.

9. The compound of claim 1, wherein the compound is (2E)-3-(5-{[(3R)-1-(2-cyclohexylethyl)-3-pyrrolidinyl]amino}-2-pyrazinyl)-N-hydroxyacrylamide dihydrochloride.

10. The compound of claim 1, wherein the compound is (2E)-3-(5-{[(3R)-1-(2-cyclohexylethyl)-3-piperidinyl]amino}-2-pyrazinyl)-N-hydroxyacrylamide dihydrochloride.

11. The compound of claim 1, wherein the compound is (2E)-3-(5-{[(3R)-1-(3-cyclohexylpropyl)-3-pyrrolidinyl]amino}-2-pyrazinyl)-N-hydroxyacrylamide dihydrochloride.

12. The compound of claim 1, wherein the compound is (2E)-3-[5-({(3R)-1-[2-(3-fluorophenyl)ethyl]-3-pyrrolidinyl}amino)-2-pyrazinyl]-N-hydroxyacrylamide dihydrochloride.

13. The compound of claim 1, wherein the compound is (2E)-3-[5-({(3R)-1-[2-(3-fluorophenyl)ethyl]-3-piperidinyl}amino)-2-pyrazinyl]-N-hydroxyacrylamide dihydrochloride.

14. The compound of claim 1, wherein the compound is (2E)-3-[5-({(3R)-1-[2-(2-fluorophenyl)ethyl]-3-piperidinyl}amino)-2-pyrazinyl]-N-hydroxyacrylamide dihydrochloride.

15. The compound of claim 1, wherein the compound is (2E)-3-[5-({(3R)-1-[2-(2,4-difluorophenyl)ethyl]-3-pyrrolidinyl}amino)-2-pyrazinyl]-N-hydroxyacrylamide dihydrochloride.

16. The compound of claim 1, wherein the compound is (2E)-3-[5-({(3R)-1-[2-(2,6-difluorophenyl)ethyl]-3-pyrrolidinyl}amino)-2-pyrazinyl]-N-hydroxyacrylamide dihydrochloride.

17. The compound of claim 1, wherein the compound is (2E)-3-[5-({(3R)-1-[2-(3,4-difluorophenyl)ethyl]-3-pyrrolidinyl}amino)-2-pyrazinyl]-N-hydroxyacrylamide dihydrochloride.

18. The compound of claim 1, wherein the compound is (2E)-3-[5-({(3R)-1-[2-(2,4-difluorophenyl)ethyl]-3-piperidinyl}amino)-2-pyrazinyl]-N-hydroxyacrylamide dihydrochloride.

19. The compound of claim 1, wherein the compound is (2E)-3-[5-({(3R)-1-[2-(3,4-difluorophenyl)ethyl]-3-piperidinyl}amino)-2-pyrazinyl]-N-hydroxyacrylamide dihydrochloride.

20. The compound of claim 1, wherein the compound is (2E)-3-[5-({(3R)-1-[2-(2-chlorophenyl)ethyl]-3-pyrrolidinyl}amino)-2-pyrazinyl]-N-hydroxyacrylamide dihydrochloride.

21. The compound of claim 1, wherein the compound is (2E)-3-[5-({(3R)-1-[2-(4-chlorophenyl)ethyl]-3-pyrrolidinyl}amino)-2-pyrazinyl]-N-hydroxyacrylamide dihydrochloride.

22. The compound of claim 1, wherein the compound is (2E)-3-[5-({(3R)-1-[2-(2-chlorophenyl)ethyl]-3-piperidinyl}amino)-2-pyrazinyl]-N-hydroxyacrylamide dihydrochloride.

23. The compound of claim 1, wherein the compound is (2E)-3-[5-({(3R)-1-[2-(4-chlorophenyl)ethyl]-3-piperidinyl}amino)-2-pyrazinyl]-N-hydroxyacrylamide dihydrochloride.

24. The compound of claim 1, wherein the compound is (2E)-3-[5-({(3R)-1-[2-(4-bromophenyl)ethyl]-3-pyrrolidinyl}amino)-2-pyrazinyl]-N-hydroxyacrylamide dihydrochloride.

25. The compound of claim 1, wherein the compound is (2E)-N-hydroxy-3-[5-({(3R)-1-[2-(4-methoxyphenyl)ethyl]-3-pyrrolidinyl}amino)-2-pyrazinyl]acrylamide dihydrochloride.

26. The compound of claim 1, wherein the compound is (2E)-N-hydroxy-3-(5-{[(3R)-1-(3-phenylpropyl)-3-piperidinyl]amino}-2-pyrazinyl)acrylamide dihydrochloride.

27. The compound of claim 1, wherein the compound is (2E)-N-hydroxy-3-(5-{[(3R)-1-(2-methyl-2-phenylpropyl)-3-pyrrolidinyl]amino}-2-pyrazinyl)acrylamide dihydrochloride.

28. The compound of claim 1, wherein the compound is (2E)-N-hydroxy-3-(5-{[(3R)-1-(1-naphthylmethyl)-3-pyrrolidinyl]amino}-2-pyrazinyl)acrylamide dihydrochloride.

29. The compound of claim 1, wherein the compound is (2E)-N-hydroxy-3-[5-({(3R)-1-[2-(2-thienyl)ethyl]-3-pyrrolidinyl}amino)-2-pyrazinyl]acrylamide dihydrochloride.

30. The compound of claim 1, wherein the compound is (2E)-N-hydroxy-3-(5-{[(3R)-1-(7-oxabicyclo[2.2.1]hept-1-ylmethyl)-3-pyrrolidinyl]amino}-2-pyrazinyl)acrylamide dihydrochloride.

* * * * *